US011911180B2

(12) United States Patent
Fu et al.

(10) Patent No.: US 11,911,180 B2
(45) Date of Patent: *Feb. 27, 2024

(54) SENSING GARMENT AND METHOD FOR MAKING SAME

(71) Applicant: Siren Care, Inc., San Francisco, CA (US)

(72) Inventors: Jie Fu, Shanghai (CN); Xuening Shen, Shanghai (CN)

(73) Assignee: Siren Care, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/378,208

(22) Filed: Jul. 16, 2021

(65) Prior Publication Data

US 2022/0175317 A1    Jun. 9, 2022

Related U.S. Application Data

(63) Continuation of application No. 16/836,800, filed on Mar. 31, 2020, now Pat. No. 11,109,807, which is a
(Continued)

(30) Foreign Application Priority Data

Dec. 14, 2018   (WO) ................ PCT/CN2018/121244

(51) Int. Cl.
*A61B 5/00*          (2006.01)
*A41B 11/00*         (2006.01)
(Continued)

(52) U.S. Cl.
CPC ............ *A61B 5/6807* (2013.01); *A41B 11/00* (2013.01); *A43B 17/00* (2013.01); *A61B 5/0008* (2013.01);
(Continued)

(58) Field of Classification Search
CPC ....... A61B 5/6807; A61B 5/0008; A61B 5/01; A61B 2562/04; A61B 2562/222;
(Continued)

(56) References Cited

U.S. PATENT DOCUMENTS

D281,081 S    10/1985  Zwissler et al.
4,670,977 A    6/1987  Scrantom et al.
(Continued)

FOREIGN PATENT DOCUMENTS

CN         1226855 A    8/1999
CN         1924131 A    3/2007
(Continued)

OTHER PUBLICATIONS

Buckley, P. (2016). Smart socks help prevent diabetes complications, smart2zero.com (online), located at https://www.smart2zero.com/news/smart-socks-help-prevent-diabetes-complications, 1 total page.
(Continued)

*Primary Examiner* — May A Abouelela
(74) *Attorney, Agent, or Firm* — Cooley LLP

(57) ABSTRACT

A system for monitoring a user includes a garment configured to be placed on a foot of the user, a cover coupled to the garment, and a sensor arrangement between the garment and the cover, wherein the sensor arrangement comprises at least one temperature sensor to measure at least one temperature on the foot of the user. A method for making a system for monitoring a user includes forming a sensor arrangement including at least one sensor lead coupled to a temperature sensor, positioning at least a portion of the sensor arrangement on a garment configured to be placed on a foot of the user, and enclosing at least the portion of the sensor arrangement between the garment and a cover.

19 Claims, 39 Drawing Sheets

Related U.S. Application Data continuation of application No. PCT/CN2019/092201, filed on Jun. 21, 2019.

(51) Int. Cl.
  *A43B 17/00* (2006.01)
  *A61B 5/01* (2006.01)
  *G01K 13/20* (2021.01)

(52) U.S. Cl.
  CPC .............. *A61B 5/01* (2013.01); *G01K 13/20* (2021.01); *A61B 2562/04* (2013.01); *A61B 2562/222* (2013.01)

(58) Field of Classification Search
  CPC ....... A61B 5/6829; A41B 11/00; A43B 17/00; G01K 13/20; A41D 1/005
  See application file for complete search history.

(56) References Cited

U.S. PATENT DOCUMENTS

| | | | |
|---|---|---|---|
| D316,119 S | 4/1991 | McDermott et al. | |
| 5,191,895 A * | 3/1993 | Koltringer | A61B 5/4824 |
| | | | 600/549 |
| 5,216,202 A | 6/1993 | Yoshida et al. | |
| 5,361,133 A | 11/1994 | Brown et al. | |
| 5,446,452 A | 8/1995 | Litton | |
| 5,546,955 A * | 8/1996 | Wilk | A61B 5/6807 |
| | | | 600/592 |
| 5,642,096 A * | 6/1997 | Leyerer | A43B 7/147 |
| | | | 73/172 |
| 5,678,566 A | 10/1997 | Dribbon | |
| 5,729,966 A | 3/1998 | Grulick | |
| 5,788,114 A | 8/1998 | Perego | |
| 5,791,134 A | 8/1998 | Schneider et al. | |
| 5,929,332 A * | 7/1999 | Brown | A43B 3/00 |
| | | | 600/592 |
| 6,195,921 B1 * | 3/2001 | Truong | A43B 3/00 |
| | | | 36/137 |
| 6,289,107 B1 | 9/2001 | Borchers et al. | |
| 6,329,917 B1 | 12/2001 | Leonard | |
| 6,398,740 B1 | 6/2002 | Lavery et al. | |
| 6,767,330 B2 * | 7/2004 | Lavery | A61B 5/015 |
| | | | 128/920 |
| 7,395,614 B1 * | 7/2008 | Bailey, Sr. | A43B 13/203 |
| | | | 36/1 |
| D589,524 S | 3/2009 | Orellana et al. | |
| 7,592,276 B2 | 9/2009 | Hill et al. | |
| 7,716,005 B2 | 5/2010 | Shoureshi et al. | |
| 8,360,987 B2 | 1/2013 | Kantro et al. | |
| D689,505 S | 9/2013 | Convay et al. | |
| 8,536,075 B2 | 9/2013 | Leonard | |
| D691,166 S | 10/2013 | Convay et al. | |
| 8,814,054 B2 | 8/2014 | Brun et al. | |
| 8,925,392 B2 * | 1/2015 | Esposito | G01L 1/18 |
| | | | 73/862.01 |
| D732,055 S | 6/2015 | Schwartz | |
| 9,186,092 B2 * | 11/2015 | Mestrovic | A61B 5/1121 |
| 9,326,723 B2 | 5/2016 | Petersen et al. | |
| 9,743,861 B2 | 8/2017 | Giedwoyn et al. | |
| 9,756,895 B2 | 9/2017 | Rice et al. | |
| 10,004,428 B2 * | 6/2018 | Everett | A61B 5/72 |
| D822,053 S | 7/2018 | Linders et al. | |
| 10,026,292 B2 * | 7/2018 | Baker | G08B 21/043 |
| 10,159,440 B2 | 12/2018 | Longinotti-Buitoni et al. | |
| D837,237 S | 1/2019 | Fraser et al. | |
| 10,292,652 B2 * | 5/2019 | Berg | A61B 5/1112 |
| 10,301,751 B2 | 5/2019 | Dias et al. | |
| 10,306,687 B2 * | 5/2019 | Folske | G06F 1/163 |
| 10,321,832 B2 * | 6/2019 | Berg | A61B 5/1118 |
| 10,327,700 B2 * | 6/2019 | Lee | A43B 3/34 |
| 10,398,376 B2 * | 9/2019 | Berg | H01R 12/774 |
| 10,480,104 B2 * | 11/2019 | Fu | D02G 3/441 |
| 10,557,220 B2 | 2/2020 | Fu et al. | |
| 10,602,932 B2 | 3/2020 | Ma et al. | |
| 10,638,937 B2 | 5/2020 | Ma et al. | |
| 10,687,562 B2 * | 6/2020 | Donohoe | A61B 5/681 |
| D916,834 S | 4/2021 | Cone et al. | |
| 11,103,699 B1 | 8/2021 | Oppenheim et al. | |
| 11,109,807 B2 | 9/2021 | Fu et al. | |
| 11,147,510 B2 * | 10/2021 | McMillen | G01L 1/2293 |
| D950,400 S | 5/2022 | Fu et al. | |
| 11,447,896 B2 | 9/2022 | Fu et al. | |
| 11,627,883 B2 | 4/2023 | Linders et al. | |
| 2002/0082486 A1 * | 6/2002 | Lavery | A61B 5/01 |
| | | | 600/300 |
| 2002/0195442 A1 | 12/2002 | Lee | |
| 2004/0009729 A1 | 1/2004 | Hill et al. | |
| 2005/0049816 A1 | 3/2005 | Oda et al. | |
| 2005/0070778 A1 | 3/2005 | Lackey et al. | |
| 2005/0171456 A1 | 8/2005 | Hirschman et al. | |
| 2007/0194130 A1 | 8/2007 | Bauer | |
| 2007/0246334 A1 * | 10/2007 | Elkins | A61F 2/68 |
| | | | 600/300 |
| 2008/0109183 A1 | 5/2008 | Shoureshi et al. | |
| 2008/0214962 A1 | 9/2008 | Kantro et al. | |
| 2009/0053950 A1 | 2/2009 | Surve | |
| 2009/0076772 A1 | 3/2009 | Hinshaw et al. | |
| 2009/0139198 A1 | 6/2009 | Dias et al. | |
| 2010/0185398 A1 * | 7/2010 | Berns | A61B 5/6804 |
| | | | 726/28 |
| 2010/0261530 A1 | 10/2010 | Thomas et al. | |
| 2010/0324455 A1 | 12/2010 | Rangel et al. | |
| 2011/0015498 A1 * | 1/2011 | Mestrovic | A61B 5/6807 |
| | | | 600/592 |
| 2011/0054359 A1 * | 3/2011 | Sazonov | A61B 5/1118 |
| | | | 600/595 |
| 2011/0214501 A1 * | 9/2011 | Ross | A61B 5/6807 |
| | | | 73/172 |
| 2012/0109013 A1 * | 5/2012 | Everett | A61B 5/1038 |
| | | | 600/587 |
| 2013/0002533 A1 | 1/2013 | Burroughs et al. | |
| 2013/0053677 A1 | 2/2013 | Schoenfeld | |
| 2013/0072765 A1 | 3/2013 | Kahn et al. | |
| 2013/0092742 A1 | 4/2013 | Brun et al. | |
| 2013/0137943 A1 * | 5/2013 | Pinto Rodrigues | A61B 5/4866 |
| | | | 600/595 |
| 2013/0145588 A1 | 6/2013 | Nakata | |
| 2013/0166079 A1 | 6/2013 | Wilhelm et al. | |
| 2013/0185003 A1 * | 7/2013 | Carbeck | A61B 5/6829 |
| | | | 702/41 |
| 2013/0192071 A1 * | 8/2013 | Esposito | A43B 17/00 |
| | | | 324/693 |
| 2013/0211281 A1 | 8/2013 | Ross et al. | |
| 2013/0213145 A1 * | 8/2013 | Owings | G01L 1/225 |
| | | | 73/862.046 |
| 2013/0213147 A1 | 8/2013 | Rice et al. | |
| 2013/0258085 A1 | 10/2013 | Leedy et al. | |
| 2013/0261494 A1 * | 10/2013 | Bloom | A61B 5/0022 |
| | | | 600/549 |
| 2014/0121479 A1 | 5/2014 | O'Connor et al. | |
| 2014/0121532 A1 | 5/2014 | O'Connor et al. | |
| 2014/0142396 A1 | 5/2014 | Ricks et al. | |
| 2014/0222173 A1 | 8/2014 | Giedwoyn et al. | |
| 2014/0268099 A1 | 9/2014 | Moslehi | |
| 2014/0276235 A1 * | 9/2014 | Raniere | A61B 5/486 |
| | | | 600/592 |
| 2014/0288669 A1 | 9/2014 | Sanders et al. | |
| 2014/0378786 A1 | 12/2014 | Hong et al. | |
| 2015/0025332 A1 * | 1/2015 | Yang | A61B 5/1121 |
| | | | 600/587 |
| 2015/0057562 A1 * | 2/2015 | Linders | A43B 3/34 |
| | | | 600/549 |
| 2015/0094544 A1 | 4/2015 | Spolin et al. | |
| 2015/0105687 A1 | 4/2015 | Abreu | |
| 2015/0157263 A1 | 6/2015 | Workman et al. | |
| 2015/0173666 A1 * | 6/2015 | Smith | A61B 5/11 |
| | | | 600/595 |
| 2015/0173679 A1 * | 6/2015 | West | A61B 5/6803 |
| | | | 600/549 |
| 2015/0177080 A1 | 6/2015 | Esposito et al. | |
| 2015/0190059 A1 | 7/2015 | Petersen et al. | |

(56) References Cited

U.S. PATENT DOCUMENTS

| | | | |
|---|---|---|---|
| 2015/0201846 A1* | 7/2015 | Maiershon | G16H 40/67 |
| | | | 600/301 |
| 2015/0297100 A1* | 10/2015 | Castillo | A61B 5/02055 |
| | | | 600/301 |
| 2015/0351493 A1 | 12/2015 | Ashcroft et al. | |
| 2015/0359457 A1 | 12/2015 | Blumenthal et al. | |
| 2016/0011091 A1* | 1/2016 | Huang | A61B 5/7228 |
| | | | 73/841 |
| 2016/0038037 A1 | 2/2016 | Kovacs | |
| 2016/0066821 A1 | 3/2016 | Mestrovic et al. | |
| 2016/0100720 A1 | 4/2016 | Holguin | |
| 2016/0135743 A1* | 5/2016 | Cobbett | G01C 21/3697 |
| | | | 2/243.1 |
| 2016/0180447 A1 | 6/2016 | Kamalie et al. | |
| 2016/0192862 A1* | 7/2016 | Merrell | A61B 5/1038 |
| | | | 600/592 |
| 2016/0206242 A1* | 7/2016 | Esposito | A61B 5/1038 |
| 2016/0249174 A1 | 8/2016 | Patel et al. | |
| 2016/0256706 A1 | 9/2016 | Harrison | |
| 2016/0299526 A1 | 10/2016 | Inagaki et al. | |
| 2016/0338621 A1 | 11/2016 | Kanchan et al. | |
| 2016/0367191 A1* | 12/2016 | Esposito | D04B 1/14 |
| 2017/0127734 A1* | 5/2017 | Roberts | A41D 13/0015 |
| 2017/0188841 A1* | 7/2017 | Ma | A61B 5/0008 |
| 2017/0188950 A1 | 7/2017 | Gazdag et al. | |
| 2017/0231551 A1 | 8/2017 | Fleischer et al. | |
| 2017/0273569 A1 | 9/2017 | Barber et al. | |
| 2017/0275789 A1 | 9/2017 | Dias et al. | |
| 2017/0333256 A1 | 11/2017 | Bassez et al. | |
| 2017/0339524 A1 | 11/2017 | Cho et al. | |
| 2017/0345279 A1 | 11/2017 | Abraham et al. | |
| 2018/0000367 A1 | 1/2018 | Longinotti-Buitoni | |
| 2018/0003579 A1* | 1/2018 | Esposito | D04B 1/26 |
| 2018/0220962 A1 | 8/2018 | Palley et al. | |
| 2018/0295895 A1 | 10/2018 | Donohoe et al. | |
| 2018/0307314 A1* | 10/2018 | Connor | A61B 5/1123 |
| 2018/0317597 A1* | 11/2018 | Maxey | H02J 50/402 |
| 2018/0317820 A1 | 11/2018 | Pace et al. | |
| 2019/0094088 A1* | 3/2019 | Reif | A61B 5/6807 |
| 2019/0283394 A1 | 9/2019 | Ashcroft et al. | |
| 2019/0313913 A1 | 10/2019 | Fu et al. | |
| 2019/0320939 A1 | 10/2019 | Orvis et al. | |
| 2019/0335843 A1 | 11/2019 | Lu et al. | |
| 2020/0000180 A1 | 1/2020 | Sherrah et al. | |
| 2020/0222001 A1 | 7/2020 | Fu et al. | |
| 2020/0245724 A1 | 8/2020 | Kobe et al. | |
| 2020/0253482 A1 | 8/2020 | Ma et al. | |
| 2020/0289028 A1* | 9/2020 | Oumnia | H04W 4/023 |
| 2020/0353239 A1* | 11/2020 | Daniels | A61N 1/02 |
| 2020/0375470 A1 | 12/2020 | Fu et al. | |
| 2020/0385895 A1 | 12/2020 | Fu et al. | |
| 2021/0046356 A1 | 2/2021 | Czaja et al. | |
| 2021/0077304 A1* | 3/2021 | Xu | A61B 5/447 |
| 2021/0145622 A1* | 5/2021 | Riffel | A43B 13/186 |
| 2021/0298674 A1 | 9/2021 | Fu et al. | |
| 2022/0389626 A1 | 12/2022 | Fu et al. | |
| 2023/0240542 A1 | 8/2023 | Linders et al. | |

FOREIGN PATENT DOCUMENTS

| | | |
|---|---|---|
| CN | 101411551 A | 4/2009 |
| CN | 203914881 U | 11/2014 |
| CN | 104746194 A | 7/2015 |
| CN | 104766116 A | 7/2015 |
| CN | 105030248 A | 11/2015 |
| CN | 105188533 A | 12/2015 |
| CN | 106132291 A | 11/2016 |
| CN | 107669247 A | 2/2018 |
| CN | 108471946 A | 8/2018 |
| CN | 108697341 A | 10/2018 |
| DE | 10 2011 012 458 A1 | 8/2012 |
| EP | 2 591 717 B1 | 8/2016 |
| GB | 2 426 255 A | 11/2006 |
| GB | 2 472 025 A | 1/2011 |
| GB | 2472026 A | 1/2011 |
| JP | 2008-138350 A | 6/2008 |
| WO | WO-02/095839 A2 | 11/2002 |
| WO | WO-02/095839 A3 | 11/2002 |
| WO | WO-2008/080245 A2 | 7/2008 |
| WO | WO-2008/080245 A3 | 7/2008 |
| WO | WO-2009/005373 A1 | 1/2009 |
| WO | WO-2011/010093 A1 | 1/2011 |
| WO | WO-2014/179343 A1 | 11/2014 |
| WO | WO-2015/143218 A1 | 9/2015 |
| WO | WO-2016/038342 A1 | 3/2016 |
| WO | WO-2017/048979 A1 | 3/2017 |
| WO | WO-2017/079628 A1 | 5/2017 |
| WO | WO-2017/106760 A1 | 6/2017 |
| WO | WO-2017/115083 A1 | 7/2017 |
| WO | WO-2017/120063 A1 | 7/2017 |
| WO | WO-2017/172781 A1 | 10/2017 |
| WO | WO-2017/175001 A1 | 10/2017 |
| WO | WO-2018/064174 A1 | 4/2018 |

OTHER PUBLICATIONS

Buhr, S. (2016). Siren Care makes a "smart" sock to track diabetic health, techcrunch.com (online), located at https://techcrunch.com/2016/11/25/siren-care-makes-a-smart-sock-to-track-diabetic-health/, 2 total pages.

Corrected Notice of Allowability dated Mar. 2, 2020, for U.S. Appl. No. 15/382,248, filed Dec. 16, 2016, 2 pages.

Corrected Notice of Allowability dated Apr. 8, 2020, for U.S. Appl. No. 16/221,340, filed Dec. 14, 2018, 3 pages.

Extended European Search Report dated Apr. 9, 2019, for EP Application No. 16 876 847.1, filed on Dec. 16, 2016, 11 pages.

Extended European Search Report dated Aug. 21, 2020, for EP Application No. 17 857 336.6, filed on Sep. 27, 2017, 9 pages.

Extended European Search Report dated Sep. 3, 2021, for EP Application No. 19 757 800.8, filed on Feb. 20, 2019, 11 pages.

Final Office Action dated Jul. 12, 2019, for U.S. Appl. No. 16/221,340, filed Dec. 14, 2018, 13 pages.

Final Office Action dated Oct. 19, 2020, for U.S. Appl. No. 16/836,800, filed Mar. 31, 2020, 14 pages.

Final Office Action dated Sep. 10, 2021, for U.S. Appl. No. 16/381,818, filed Apr. 11, 2019, 16 pages.

Hardy, D.A. et al. (2019). "Automated insertion of package dies onto wire and into a textile yarn sheath," Microsystem Technologies, pp. 1-13.

Hughes-Riley, T. et al. (2017). "A Study of Thermistor Performance within a Textile Structure," Sensors 17:1804, 14 total pages.

International Search Report dated Mar. 27, 2017, for PCT Application Number PCT/US2016/067344, filed on Dec. 16, 2016, 3 pages.

International Search Report dated Feb. 6, 2018, for PCT Application No. PCT/US2017/053738, filed on Sep. 27, 2017, 4 pages.

International Search Report dated May 1, 2019, for PCT Application No. PCT/US2019/018714, filed on Feb. 20, 2019, 2 pages.

International Search Report dated Aug. 6, 2019, for PCT Application No. PCT/US2019/027050, filed on Apr. 11, 2019, 4 pages.

International Search Report dated Sep. 10, 2019, for PCT Application No. PCT/CN2018/0121244, filed on Dec. 14, 2018, 6 pages.

International Search Report dated Aug. 27, 2019, for PCT Application No. PCT/CN2019/092201, filed on Jun. 21, 2019, 5 pages.

International Search Report dated Aug. 28, 2019, for PCT Application No. PCT/CN2018/121246, filed on Dec. 14, 2018, 5 pages.

Introducing Siren's Diabetic Socks and Foot Monitoring System (2018). Youtube.com (online), accessed Jul. 19, 2021, available online at https://www.youtube.com/watch?v=ljMZu-PiSx4 (copy of video not available).

Medical and Health Care Icon Set (2017). iconfinder.com (online), accessed Aug. 3, 2021, available at https://www.iconfinder.com/iconsets/medical-health-care-flat.

Nashed, M-N. et al. (2019). "A novel method for embedding semiconductor dies within textile yarn to create electronic textiles," Fibers 7:12, 17 total pages.

(56) References Cited

OTHER PUBLICATIONS

Non-Final Office Action dated Mar. 4, 2019, for U.S. Appl. No. 16/221,340, filed Dec. 14, 2018, 17 pages.
Non-Final Office Action dated Jul. 8, 2019, for U.S. Appl. No. 15/382,248, filed Dec. 16, 2016, 21 pages.
Non-Final Office Action dated May 21, 2020, for U.S. Appl. No. 16/836,800, filed Mar. 31, 2020, 16 pages.
Non-Final Office Action dated Apr. 29, 2021, for U.S. Appl. No. 16/381,818, filed Apr. 11, 2019, 18 pages.
Non-Final Office Action dated Jul. 28, 2021, for U.S. Appl. No. 16/737,753, filed Jan. 8, 2020, 9 pages.
Non-Final Office Action dated Aug. 23, 2021, for U.S. Appl. No. 29/694,472, filed Jun. 11, 2019, 13 pages.
Notice of Allowance dated May 30, 2019, for U.S. Appl. No. 15/717,473, filed Sep. 27, 2017, 9 pages.
Notice of Allowance dated Oct. 31, 2019, for U.S. Appl. No. 15/717,473, filed Sep. 27, 2017, 5 pages.
Notice of Allowance dated Sep. 10, 2019, for U.S. Appl. No. 15/717,498, filed Sep. 27, 2017, 14 pages.
Notice of Allowance dated Jan. 2, 2020, for U.S. Appl. No. 15/382,248, filed Dec. 16, 2016, 17 pages.
Notice of Allowance dated Jan. 8, 2020, for U.S. Appl. No. 16/221,340, filed Dec. 14, 2018, 12 pages.
Notice of Allowance dated Oct. 15, 2020, for U.S. Appl. No. 29/694,472, filed Jun. 11, 2019, 14 pages.
Notice of Allowance dated May 18, 2021, for U.S. Appl. No. 16/836,800, filed Mar. 31, 2020, 9 pages.
Notice of Allowance dated Jan. 5, 2022, for U.S. Appl. No. 29/730,291, filed Apr. 2, 2020, 9 pages.
Notice of Allowance dated Jan. 14, 2022, for U.S. Appl. No. 29/730,291, filed Apr. 2, 2020, 3 pages.
Notice of Allowance dated Feb. 18, 2022, for U.S. Appl. No. 16/737,753, filed Jan. 8, 2020, 5 pages.
Written Opinion of the International Searching Authority dated Mar. 27, 2017, for PCT Application No. PCT/US2016/067344, filed on Dec. 16, 2016, 8 pages.
Written Opinion of the International Searching Authority dated Feb. 6, 2018, for PCT Application No. PCT/US2017/053738, filed on Sep. 27, 2017, 10 pages.
Written Opinion of the International Searching Authority dated May 1, 2019, for PCT Application No. PCT/US2019/018714, filed on Feb. 20, 2019, 4 pages.
Written Opinion of the International Searching Authority dated Aug. 6, 2019, for PCT Application No. PCT/US2019/027050, filed on Apr. 11, 2019, 9 pages.
Written Opinion of the International Searching Authority dated Sep. 10, 2019, for PCT Application No. PCT/CN2018/0121244, filed on Dec. 14, 2018, 5 pages.
Written Opinion of the International Searching Authority dated Aug. 27, 2019, for PCT Application No. PCT/CN2019/092201, filed on Jun. 21, 2019, 4 pages.
Written Opinion of the International Searching Authority dated Aug. 28, 2019, for PCT Application No. PCT/CN2018/121246, filed on Dec. 14, 2018, 4 pages.
Extended European Search Report dated Jun. 5, 2023, for EP Application No. 19 896 007.2, filed on Jun. 21, 2019, 11 pages.
Non-Final Office Action dated Sep. 6, 2022, for U.S. Appl. No. 16/840,157, filed Apr. 30, 2020, 15 pages.
Non-Final Office Action dated Apr. 5, 2022, for U.S. Appl. No. 16/381,818, filed Apr. 11, 2019, 14 pages.
Notice of Allowance dated Sep. 21, 2023, for U.S. Appl. No. 17/887,374, filed Aug. 12, 2022, 9 pages.

* cited by examiner

SENSING GARMENT AND METHOD FOR MAKING SAME

CROSS-REFERENCE TO RELATED APPLICATIONS

This application is a continuation of U.S. patent application Ser. No. 16/836,800, filed on Mar. 31, 2020, now U.S. Pat. No. 11,109,807, which claims priority to PCT Application No. PCT/CN2019/092201, filed on Jun. 21, 2019, which claims priority to PCT Application No. PCT/CN2018/121244, filed on Dec. 14, 2018, each of which is hereby incorporated by reference in its entirety.

TECHNICAL FIELD

This invention relates generally to the field of foot care and more specifically to new and useful sensing garments and methods for making the same.

BACKGROUND

Diabetes is an increasingly common medical condition in which the body has an impaired ability to produce or respond to the hormone insulin. Diabetes damages blood vessels and nerves, particularly in the feet, and can lead to severe medical complications that are difficult to treat. For example, one complication of poorly controlled diabetes is foot ulcers, which may fail to heal because of poor blood circulation in diabetics and because treatment does not always successfully halt the spread of infection. Diabetic foot ulcers are painful and, when unresolved, can lead to lower limb amputations. As another example, Charcot foot, also known as Charcot arthropathy, is a debilitating complication of diabetes involving fractures and dislocations of bones and joints that occur with minimal or no known trauma.

Self-care is critical to detecting early signs of ulcers, Charcot foot, and other injuries and allowing timely treatment. However, visual inspection for detecting such conditions has limitations. For example, obese or visually impaired patients may not be able to see their feet easily. Additionally, due to neuropathy (numbness or loss of feeling as a result of nerve damage) caused by diabetes, a patient may not be able to feel early development of a foot ulcer and/or fractures. Even further, X-rays are unable to reliably show early stages of fractures. Accordingly, painful and dangerous foot conditions may be detected only when they have progressed to a more severe state, which increases the likelihood of extreme treatments such as amputation.

Thus, there is a need for new and improved systems and methods for monitoring the feet health of patients.

SUMMARY

Generally, a system for monitoring a user includes a garment configured to be placed on a foot of the user, a cover coupled to the garment, and a sensor arrangement between the garment and the cover, wherein the sensor arrangement comprises at least one temperature sensor to measure at least one temperature on the foot of the user. In some variations, the garment may include a sole region (e.g., plantar region) and the sensor arrangement may be between the sole region of the garment and the cover. The garment may, for example, include a sock or a shoe insole.

The sensor arrangement may include a plurality of sensor leads, where each sensor lead is coupled to a respective temperature sensor. The sensor leads may be arranged in a bundle, such as a flattened bundle, for traversing the garment (e.g., at least the sole region or plantar region of the garment). For example, the bundle of sensor leads may be shaped to follow a curved path. In some variations, one or more sensor leads may include a distal portion that diverges from the sensor lead bundle so as to separately position its associated temperature sensor at a desired measurement location on the garment. In some variations, at least a portion of the bundle may be sealed within a film such as a thermoplastic. In some variations, the sensor arrangement may be received in a recessed portion in the sole region of the garment, which can, for example, reduce the resulting profile of the assembled system and reduce discomfort and/or injury to a user wearing the garment.

The temperature sensors in the sensor arrangement may be arranged in various suitable patterns on the garment. In one exemplary variation, the sensor arrangement includes at least one temperature sensor arranged on the sole region at a location selected from an ossa digit region of the garment, between a phalange region and a metatarsal region of the garment, between the metatarsal region of the garment and a tarsal region of the garment, and a heel region of the garment.

Furthermore, in some variations, the garment may further include a housing, where the housing encloses a proximal portion of the sensor arrangement. The housing may further enclose at least one of a controller, a wireless communication module, a power supply, and a memory.

The cover may be coupled to the sole region around a perimeter of at least a portion of the sensor arrangement and/or housing, thereby enclosing the sensor arrangement and/or housing between the garment and the cover. In some variations, the cover may include a textile and configured to be heat sealed to the garment.

Generally, a method for making a user monitoring system includes forming a sensor arrangement comprising at least one sensor lead, wherein the sensor lead is coupled to a temperature sensor, positioning at least a portion of the sensor arrangement on a garment configured to be placed on a foot of the user, and enclosing at least the portion of the sensor arrangement between the garment and a cover. In some variations, the method may further include removing material from the sole region of the garment to form a recessed portion of the sole region, such that at least a portion of the sensor arrangement may be positioned in the recessed portion of the sole region. The garment may, for example, include a sock or a shoe insole.

In some variations, the sensor arrangement may be formed into a grouped bundle of sensor leads, each with a respective temperature sensor. For example, the sensor arrangement may be formed into a flattened bundle. The bundle may take various shapes. For example, the bundle may be shaped to follow a curved path. In some variations, forming the sensor arrangement may include arranging at least one sensor lead such that its distal portion and its respective temperature sensor diverges from the bundle to positioning the temperature sensor at a desired measurement location. In some variations, the method may include sealing the sensor arrangement within a film such as a thermoplastic.

In some variations, enclosing at least a portion of the sensor arrangement includes coupling the cover to the garment. For example, coupling the cover to the garment may include coupling the cover to the sole region around a perimeter of at least a portion of the sensor arrangement. Such coupling may be performed with heat sealing, for example. In some variations, the method may further include enclosing a proximal portion of the sensor arrangement in a housing, and coupling the housing to the garment.

Systems for monitoring a user may include a garment configured to be placed adjacent a body part of a user, a cover coupled to the garment, and a sensor arrangement between the garment and the cover, wherein the sensor arrangement comprises at least one sensor to measure at least one parameter associated with the body part of the user. The at least one parameter measured by the sensor may be any suitable parameter. For example, the at least one parameter measured by the sensor may be temperature, pressure, moisture, strain, user activity, muscle activity, motion, the amount of time the garment is worn, orientation, etc. Furthermore, the garment may, for example, include a sock or a shoe insole. In some variations, the sensor arrangement may include a plurality of sensor leads, where each sensor lead is coupled to a respective sensor. For example, the garment may include a sole region, and the sensor arrangement may be between the sole region of the garment and the cover. The cover may be coupled to the sole region around a perimeter of at least a portion of the sensor arrangement. The cover may be heat sealed to the garment. In some variations, the sensor leads may be arranged in a flattened bundle traversing the garment. For example, the bundle may be shaped to follow a curved path along the garment. In some variations, at least a portion of the bundle may be sealed within flexible film. Sensors may be distributed along the sole region of the garment in any suitable manner. In some variations, the sensor arrangement may comprise at least one sensor arranged on the sole region at a location selected from an ossa digit region of the garment, between a phalange region and a metatarsal region of the garment, between the metatarsal region of the garment and a tarsal region of the garment, and a heel region of the garment.

Methods for making a user monitoring system may include forming a sensor arrangement including at least one sensor lead, where the sensor lead is coupled to a sensor for measuring at least one parameter associated with a body part of the user, positioning at least a portion of the sensor arrangement on a garment configured to be placed adjacent the body part of the user, and enclosing at least a portion of the sensor arrangement between the garment and a cover. The garment may, for example, include a sock or a shoe insole. Forming a sensor arrangement may comprise arranging the sensor leads into a flattened bundle. In some variations, methods may include shaping the bundle to follow a curved path. The at least one parameter measured by the sensor may be any suitable parameter. For example, the at least one parameter measured by the sensor may be temperature, pressure, moisture, strain, user activity, muscle activity, motion, the amount of time the garment is worn, orientation, etc.

Various methods may be used to enclose at least a portion of the sensor arrangement between the garment and the cover. For example, enclosing a portion of the sensor arrangement may comprise coupling the cover to the garment. In some variations, coupling the cover to the garment may comprise coupling the cover to the sole region around the perimeter of a portion of the sensor arrangement.

DETAILED DESCRIPTION

Figure 1A:
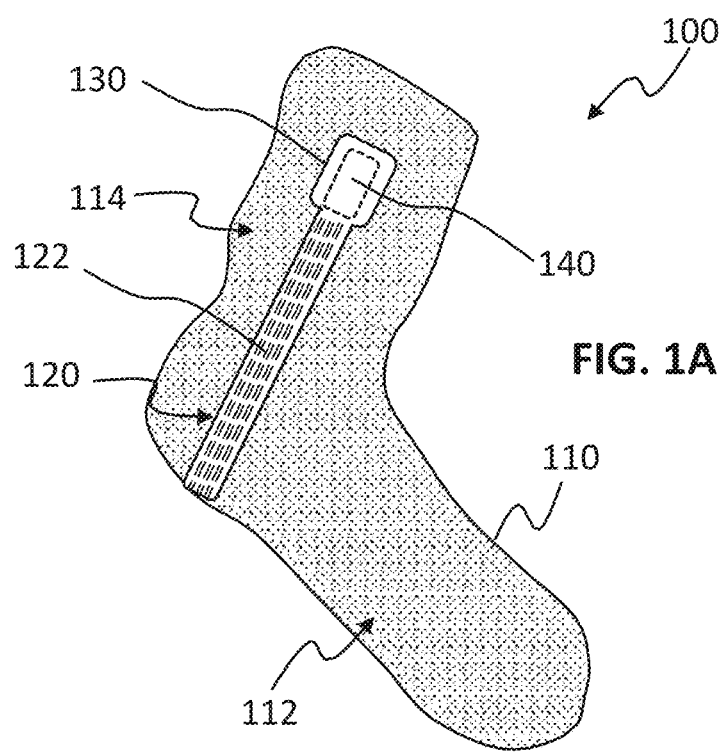
FIGS. 1A and 1B are side and bottom views, respectively, of an exemplary variation of a system for monitoring a user.

Non-limiting examples of various aspects and variations of the invention are described herein and illustrated in the accompanying drawings.

Generally, described herein are various systems for monitoring a user and methods for making such systems. The system may be a garment (e.g., sock) worn on the foot of a user and configured to measure one or more physical characteristics of the user, such as skin temperatures at one or more locations on a foot of the user. In some variations, a user may wear two garments, including one garment on a left foot of the user, and another garment on a right foot of the user. Temperature measurements may be performed substantially continuously as the garments are worn.

For example, a diabetic user may suffer from diabetic neuropathy and consequently experience little or no feeling in the user's feet, which limits the user's ability to identify development of injuries such as sores, ulcers, infection, or poor blood circulation in the user's feet. If left untreated, such conditions may lead to greater medical complications, such as amputation of one or both feet. However, when a region of a foot becomes infected, the temperature of the affected region may generally rise as the body combats the infection. Accordingly, systems described herein, when worn, can provide temperature data that may be analyzed to assess inflammation in diabetic feet and identify and/or detect development of diabetic foot complications. In some variations, a sampled temperature differential between corresponding locations on left and right feet of the user can be compared to a baseline temperature differential between the same corresponding locations. A threshold change between the baseline and sampled temperature differential (e.g., a change of about 4° F. or more) can indicate, for example, an early sign of diabetic foot ulcers. Exemplary methods for assessing foot inflammation based on foot temperature measurements from the system are described in U.S. Patent App. Pub. No. 2017/0188841, which is hereby incorporated in its entirety by this reference.

Systems described herein can provide substantially continuous temperature measurements at various locations of the user's feet, which enable a more effective prediction and/or detection of diabetic foot conditions compared to conventional methods of assessment. Conventional methods for monitoring diabetic foot conditions include using a handheld foot thermometer to measure temperature at selected locations of the foot. Such tools are designed to measure temperatures once a day or at long intervals. However, these tools fail to provide a comprehensive temporal and spatial understanding of temperature pattern data. In contrast, continuous monitoring allows the assessment of temperature over longer periods and with more temporal resolution, such that micropatterns (e.g., over the course of an hour or through the day) can be taken into consideration when assessing for development of foot conditions in the user. For example, a once-a-day measurement may capture a temporarily normal-looking temperature characteristic of a user's foot, but fail to capture subsequent signs of inflammation later in the day as the result of the day's activities. In contrast, continuous monitoring can facilitate analysis of temperature patterns (both spatial and temporal) specific to a user, for more accurate assessments. Furthermore, the systems herein may incorporate activity data (e.g., from an accelerometer, pedometer, etc.) such that analysis can take into consideration varying levels of user activity over time (and assess how activity affects temperature patterns). Accordingly, continuous monitoring has a greater potential to report consistent and clinically relevant temperature increases. Thus, systems such as those described herein, which provide continuous temperature monitoring, have the potential to further improve home care and early detection of diabetic foot conditions. Variations of such systems, and methods for making such systems, are described in further detail below.

System for Monitoring a User

Figure 1B:
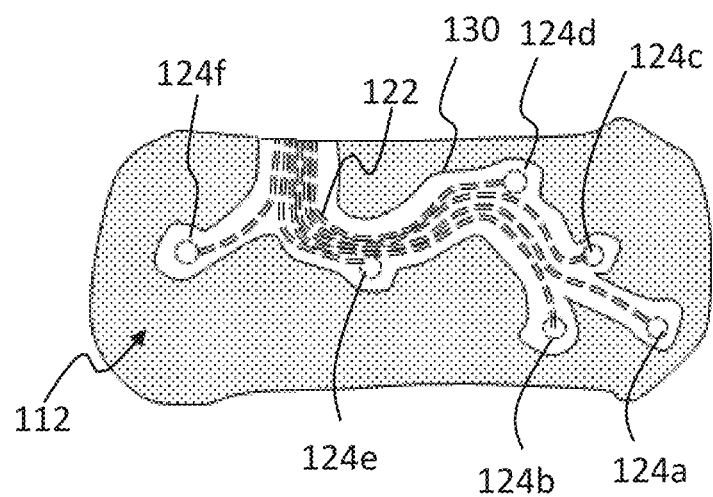

In some variations, as shown in FIGS. 1A and 1B, a system 100 for monitoring a user can include a garment 110 configured to be placed on a foot of the user where the garment may include a sole region 112, a cover 130 coupled to the garment 110, and a sensor arrangement 120 between the garment (e.g., the sole region 112 of the garment) and the cover 130, where the sensor arrangement includes at least one temperature sensor to measure at least one temperature on the foot of the user. For example, in some variations, as shown in FIG. 1B, the sensor arrangement may include a plurality of temperature sensors 124 arranged in different regions of the garment so as to measure temperature at various locations on sole of the foot of the user.

Garment

The garment of the system 100 provides a substrate or platform for the sensor arrangement, and positions the sensors relative to desired measurement locations of the user when the garment is worn. In some variations, the garment includes a sock configured to be placed or worn on a foot of the user. However, the garment may alternatively be any suitable component to be positioned on the foot such as a shoe, a slipper, an insole, etc. For example, in some variations, a garment may be a shoe or shoe component configured to house a sensor arrangement. For example, the shoe may include an insole configured to receive one or more sensor arrangements. The insole may include one or more sensor arrangements coupled to the insole by a cover. The garment may be configured specifically for a left foot (e.g., include a toe box accommodating contours of a left foot), for a right foot (e.g., include a toe box accommodating contours of a right foot), or may be universally or suitable for both feet. The garment may include one or more labels that are sewn, woven, or otherwise incorporated into or coupled to the garment. Examples of labels include an indication of left or right foot compatibility, size (e.g., small, medium, large, or numeric size), or other identifying info.

Furthermore although the methods and systems are primarily described herein with respect to a foot garment, it should be understood that in other variations, the garment may be any suitable garment (e.g. pants, short pants, tights, leggings, leg warmer, shirt, arm warmer, glove, mitten, scarf, hat, headband, etc.) configured to be placed adjacent to one or more suitable body parts of the user for monitoring.

As shown in FIG. 1A, in some variations, the garment 110 may include a sole region 112 (e.g. plantar region) configured to receive a foot of a user, and an ankle region 114 extending from the sole region 112. At least the sole region 112 may include a flexible material such as a textile (e.g., polyester, cotton, etc.) that is configured to conform to the foot of the user, such that when the garment is worn, temperature sensors coupled to the sole region of the garment may be positioned closely adjacent to skin of the user for providing accurate skin temperature measurements. The ankle region 114 may also include a flexible material such as textile that is configured to conform to the lower leg of the user. Additionally or alternatively, the ankle region 114 (and/or other regions of the garment such as medial or lateral aspects of the foot portion of the garment, a top or dorsal region of the foot portion of garment, etc.) may include one or more temperature sensors for providing skin temperature measurements (and/or other kinds of sensors). For example, one or more sensors may be arranged on the garment so as to measure skin temperature of the ankle and/or leg (e.g., lower leg).

In some variations, the sole region 112 and/or the ankle region 114 may include one or more recessed portions for receiving at least a portion of the sensor arrangement. The recessed portions may be on an internal surface of the garment or on an external surface of the garment. The depth of the recessed portions may be similar to (e.g., approximately equal to) or greater than the thickness of the sensor arrangement, such that when the sensor arrangement is received in the recessed portions, the sensor arrangement does not significantly extend beyond the profile of the garment material. Accordingly, one or more recessed portions on the sole region of the garment may advantageously help reduce localized pressure points (thereby reducing development or exacerbation of foot injuries caused by the user stepping on the sensor arrangement) and/or reduce the likelihood of damage to the sensor arrangement.

The recessed portions may be formed in any suitable manner. For example, the garment may generally be made of a plush or thickened material (e.g., terry knit), which may increase user comfort, the garment may include one or more recessed portions formed by reducing some of the thickness of the material across a selected area corresponding to the eventual location of the sensor arrangement on the garment. Alternatively, the garment may be woven or knit to have varying thickness, including a thinner portion that forms the one or more recessed portions. In some variations, the one or more recessed portions may be patterned to have a shape similar to that of the sensor arrangement. For example, as shown in FIG. 1B, a recessed portion (underlying the cover 130) may generally resemble the outline or path(s) of the sensor leads 122 of the sensor arrangement. Similarly, as shown in FIG. 1A, a recessed portion (underlying the cover 130) may have a rectilinear path following the path(s) of the sensor leads 122 extending from the sole region 112 of the garment to the ankle region 114 of the garment. In other words, the outline of a recessed portion 116 may substantially correspond to the outline of the sensor arrangement. In some variations, the recessed portion 116 may extend an additional margin (e.g., at least about 0.5 cm) beyond the outline of the sensor arrangement. This additional margin may, for example, account for tolerance in the size and shape of the sensor arrangement received in the recessed portion 116, and/or enable some space for movement (e.g., flexing) of the sensor leads when the garment is stretched, repositioned, etc.

However, alternatively, the one or more recessed portions may have any suitable shape (e.g., a suitable shape extending beyond the perimeter of the sensor arrangement). For example, with reference to the variation shown in FIG. 2, a recessed portion receiving the sensor arrangement may have a generally rectangular shape, similar to the cover 230.

Housing

Figure 1C:
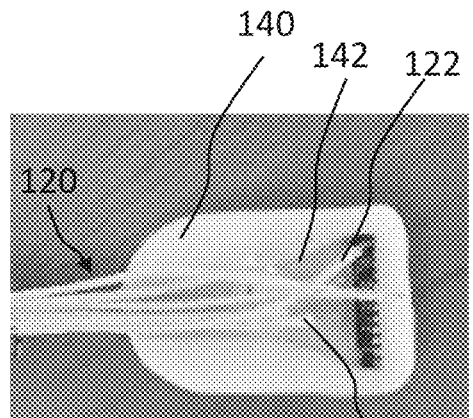
FIG. 1C is a detailed view of a portion of a sensor arrangement and a housing in an exemplary variation of a system for monitoring a user.

In some variations, the garment may further include at least one housing 140. As shown in FIG. 1C, the housing 140 may include at least one cavity 142 for receiving a proximal end of the sensor arrangement 120 as further described below, and/or housing other various components. The housing 140 may, for example, be arranged on an ankle region of the garment. In some variations, the housing 140 may be located on a lateral side of the garment. A lateral positioning of the housing may make the housing comfortable for the use (e.g., because a housing positioned on a lateral side of a garment is unlikely to interfere with walking and other activities). However, in other variations, the housing may be located on any suitable portion of the garment (e.g., medial side, anterior side, posterior side, distal side, etc.). In some variations, the housing 140 may be secured to the garment by being enclosed between the garment and a cover (similar to the sensor arrangement as described below). Additionally or alternatively, the housing may be coupled to the garment with an adhesive or mechanical fasteners (e.g., rivets, snaps, etc.), by being inserted into a pocket or other receptacle on the garment, sewn to the garment, or in any suitable manner.

The housing may be substantially sealed (e.g., hermetically sealed or waterproofed) to protect the contents of the housing from environmental conditions (e.g., when the garment is washed or worn, when the user is sweating, etc.). For example, the cavity 142 may be filled with and/or otherwise sealed with a substance adhering to the housing 140, such as ultraviolet glue, silicone, other epoxy or polymer, etc. This substance can help fix the proximal end of the sensor arrangement 120 and/or other components within the housing 140. As another example, the housing 140 may include one or more components that may be coupled together (e.g., with a suitable mechanical interfit, fasteners, weld, etc.). The joint between coupled housing components may be sealed by epoxy or other suitable sealant. In some variations, the one or more components of the housing may be formed at least in part through injection molding.

Figure 1D:
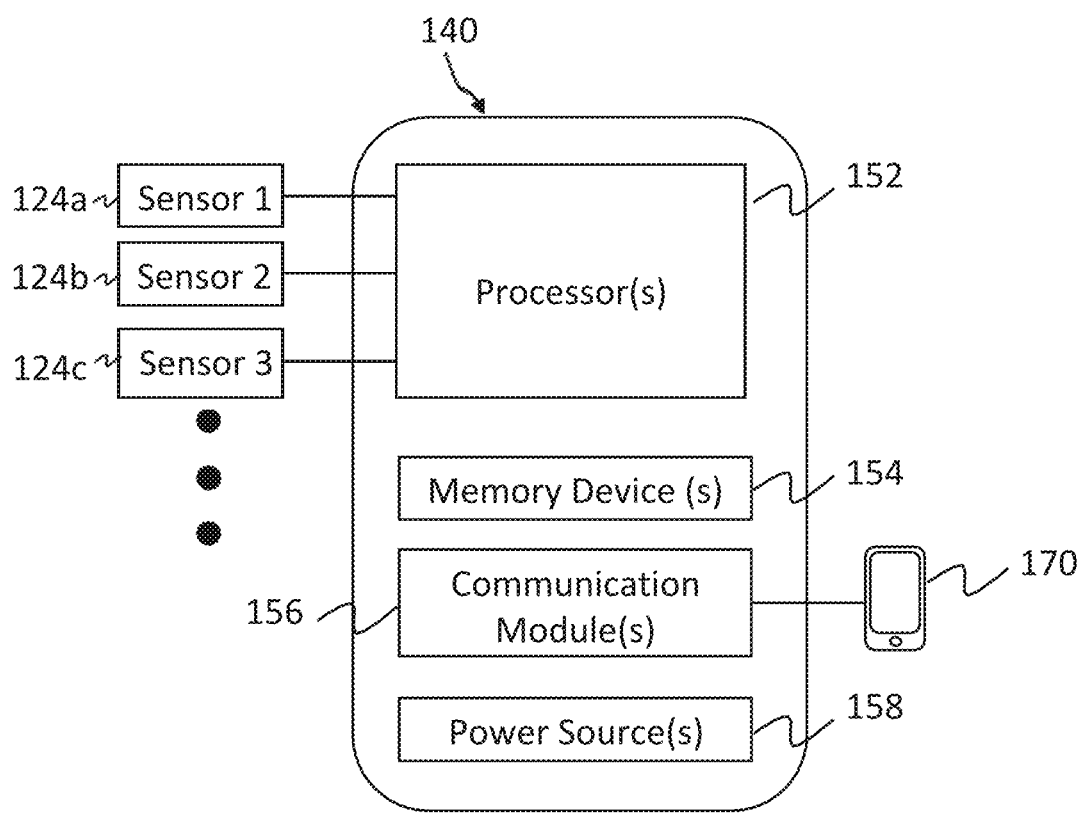
FIG. 1D is an illustrative schematic of sensors and components in a housing in an exemplary variation of a system for monitoring a user.

As shown in the schematic of FIG. 1D, the housing 140 may house various components for operating the system. For example, the housing 140 may include at least one processor 152 (e.g., CPU), at least one memory device 154 (which can include one or more computer-readable storage mediums), at least one communication module 156, and at least one power source 158. In some variations, the housing may further include one or more additional activity or other sensors (e.g., an accelerometer, a gyroscope, or an inertial measurement unit). One or more of these components may be arranged on one or more electronic circuit boards (e.g., PCBA), which in turn be mounted to the housing.

The processor 152 and memory device 154 may cooperate to provide a controller for operating the system. For example, the processor 152 may receive sensor data from one or more sensors 124 (e.g., first temperature sensor 124a, second temperature sensor 124b, third temperature sensor 124c, etc.), and the sensor data may be stored in one or more memory devices 154. In some variations, the processor 152 and memory 154 may be implemented on a single chip, while in other variations they can be implemented on separate chips.

The controller can operate in an inactive state and in an active state. The controller may, for example, toggle between the inactive state and the active state based on user input (e.g., pressing of a button) and/or sensor data (e.g., from activity sensors, processing of temperature data, etc.) suggesting placement of the garment on a user. In the inactive state, the controller may be in a "sleep" mode (e.g., to conserve energy in the power source 158). In the active state, the controller may be in an "awake" mode in which sensor data is received, processed, and/or stored in the memory device 154 for use in monitoring for inflammation. For example, in its active state, the controller may scan at least some of the temperature sensors to receive and store temperature measurement data (e.g., periodically, such as every second, every 10 seconds, every 30 seconds, every minute, every hour, or other suitable interval). Generally, the controller may operate in the inactive state when there is an indication that the garment is not being worn by the user, and may operate in the active state when there is an indication that the garment is being worn by the user. In some variations, the controller may be similar to the controller described in U.S. Patent Pub. No. 20170188841, incorporated by reference above.

The communication module 156 may be configured to communicate sensor data and/or other information to an external computing device 170. The external computing device 170 may be, for example, a mobile computing device (e.g., mobile telephone, tablet, smart watch), laptop, desktop, or other suitable computing device. The external computing device 170 may be executing a native application for presenting sensor data (and/or the results of analysis thereof) through a user interface to a user. Additionally or alternatively, the communication module 156 may be configured to communicate to one or more networked devices, such as a hub paired with the system, a server, a cloud network, etc.

The communication module 156 may communicated via a wired connection (e.g., including a physical connection such as a cable with a suitable connection interface such as USB, mini-USB, etc.) or a wireless network (e.g., through NFC, Bluetooth, WiFi, RFID, or any type of digital network that is not connected by cables). For example, devices may directly communicate with each other in pairwise connection (1:1 relationship), or in a hub-spoke or broadcasting connection ("one to many" or 1:m relationship). As another example, the devices may communicate with each other through mesh networking connections (e.g., "many to many", or m:m relationships), such as through Bluetooth mesh networking. Wireless communication may use any of a plurality of communication standards, protocols, and technologies, including but not limited to, Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (WiFi) (e.g., IEEE 802.11a, IEEE 802.11b, IEEE 802.11g, IEEE 802.11n, and the like), or any other suitable communication protocol. Some wireless network deployments may combine networks from multiple cellular networks or use a mix of cellular, Wi-Fi, and satellite communication.

Additionally, the housing may include one or more power sources 158, which may function to provide electrical power to the processor, communication module, sensors, and/or any other electrical components. For example, the power source 158 may include one or more batteries. In some variations, the power source 158 may be rechargeable such as through wireless charging methods (e.g., inductive charging, RF coupling, etc.) or by harnessing kinetic energy such as that generated through motion (e.g., when the user walks while wearing the garment).

Sensor Arrangement

As shown in FIGS. 1A and 1B, a sensor arrangement 120 may be positioned on the garment 110, such as an internal surface of the garment. The sensor arrangement 120 functions to gather measurements, including skin temperature measurements of the user, when the garment 110 is placed on the foot of the user. Although the description below references sensor arrangements including temperatures sensors, sensor arrangements may include any suitable type of sensor, such as a pressure sensor, a moisture sensor, a strain sensor, a weight sensor, a movement/activity sensor, a muscle activity (e.g., EMG) sensor, an orientation sensor, a sensor that tracks the amount of time a garment is worn (e.g., to determine compliance with a treatment plan), etc. Further, sensor arrangements may comprise more than one type of sensor (e.g., a sensor arrangement may comprise a temperature sensor and a strain sensor).

The sensor arrangement 120 may include one or more sensor leads 122, where each sensor lead is coupled to a respective temperature sensor 124. The temperature sensor 124 may be located at the distal end of its respective sensor lead. For example, the sensor arrangement 120 may include one or more thermistors, thermocouples, or other suitable temperature sensors. In some variations, some or all of the sensor leads 122 may be coated in a material such as fabric (e.g., polyester sleeve) which may, for example, increase overall strength of the sensor lead and help guard against failure due to applied stresses.

Generally, the sensor leads 122 may be grouped together (e.g., in a bundle), which may have multiple advantages. For example, compared to a single lead, the increased collective bulk (e.g., increased cross-sectional area) of the grouped sensor leads 122 may be less susceptible to stresses imparted on the sensor arrangement (e.g., when the user's weight is placed on the sensor arrangement, when the garment is stretched, etc.). Thus, the grouping or bundling of sensor leads 122 may make the sensor arrangement 120 more robust and less prone to failure. Additionally, the grouping of sensor leads 122 allows the sensor leads to be collectively manipulated with ease during assembly, thereby making assembly of the system (e.g., positioning of the sensor arrangement on the garment) easier and faster than assembly would be with individual sensor leads. In some variations, the bundle may be a flattened bundle having a low profile. For example, the group of sensor leads 122 may be arranged side-by-side in a single layer in a flattened bundle. Such a flattened bundle may, for example, may be more comfortable underfoot for the wearer of the garment.

In some variations, the sensor arrangement 120 may be positioned on the garment generally within the one or more recessed portions of the garment described above. In an exemplary variation shown in FIG. 1A, a proximal end of the sensor arrangement 120 may be received in the housing, where proximal ends of sensor leads 122 may be coupled (e.g., soldered) to respective signal-receiving pins on the processor or other components. In some variations, the sensor arrangement 120 may extend from the housing 140 along the ankle region 114 of the garment 110, wrap around the lateral side of the garment toward the sole region 112 of the garment as shown in FIG. 1B. In some variations, the sensor arrangement may wrap around a heel region of the garment as it extends toward the sole region. The sensor leads 122 may traverse the sole region 112 of the garment in any suitable path to locate the temperature sensors (at the distal ends of the sensor leads 122) at the desired measurement locations. As described in further detail below, in some variations, the sensor arrangement may be secured to the garment via the cover coupled to the garment. However, the sensor arrangement may additionally or alternatively be secured to the garment with epoxy or other adhesive, sutures, connectors or fasteners, etc.

Figure 9A:
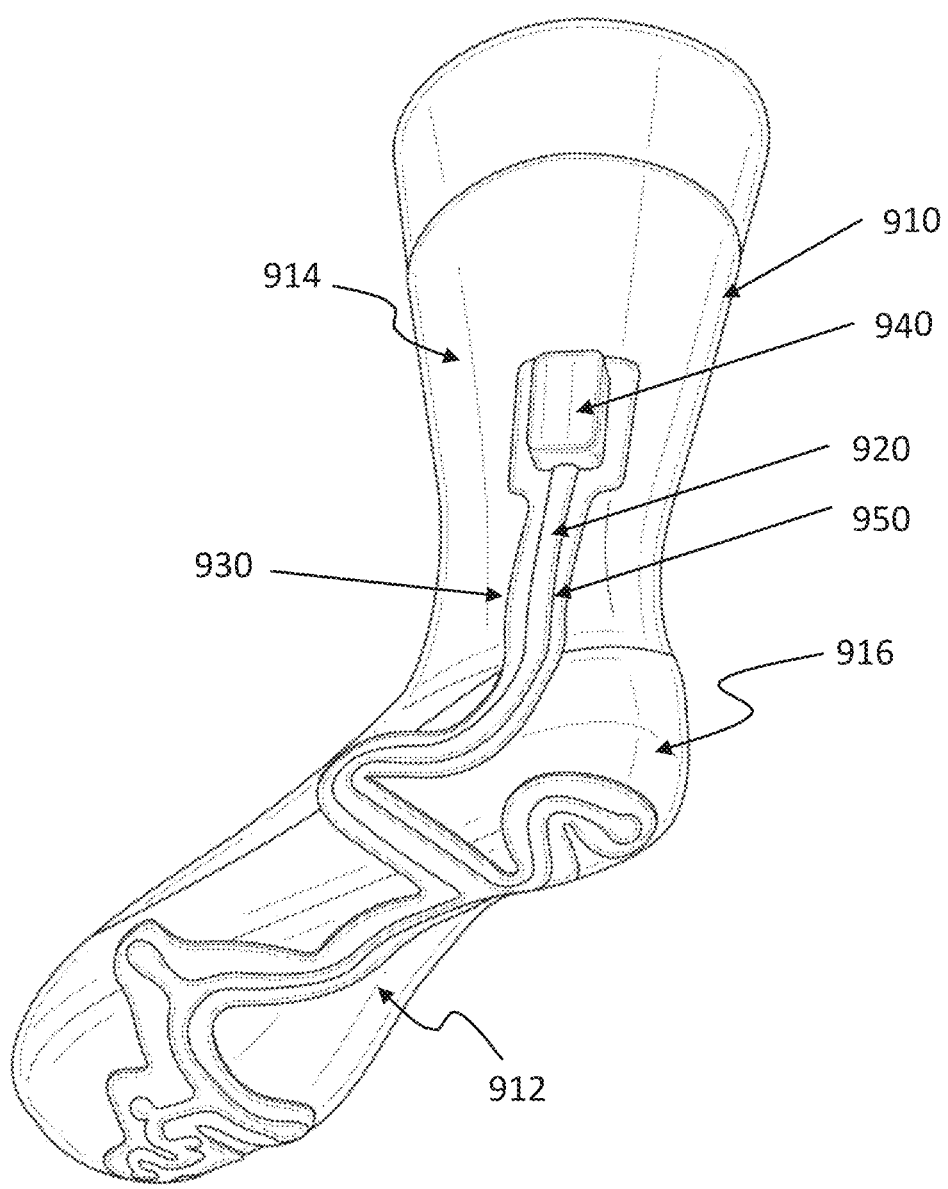
FIG. 9A is a lower perspective view of an exemplary variation of a garment.

In some variations, the sensor arrangement may form a curved path as it extends from the housing to the sole region of the garment. In an exemplary variation of a garment 910 shown in FIGS. 9A and 9B, a proximal end of the sensor arrangement 920 is received by the housing 940, and the sensor arrangement 920 extends from the housing 940 along the ankle region 914 toward the sole region 912 of the garment. In this variation, the sensor leads are grouped together in a bundle as they extend along the ankle region of the garment, and the respective sensor leads branch off to various locations along the sole region 912 of the garment (e.g., to desired sensing locations). As depicted in FIG. 9A, the sensor arrangement 920 traverses a heel region 916 of the garment in a curved configuration. The sensor arrangement 920 wraps around the heel region 916 of the garment in a substantially "S-shaped" configuration. The curved configuration of the sensor arrangement 920 may provide the benefit of reducing the strain on the sensor arrangement. For example, the curved configuration of the sensor arrangement provides excess length of sensor such that as the garment is stretched (e.g., as the user is putting the garment on or taking it off), the curved portion is straightened rather than the sensor arrangement being placed under strain. Thus, the curved portion of the sensor arrangement introduces a form of slack such that the garment can be stretched without harming the sensor arrangement.

Figure 9B:
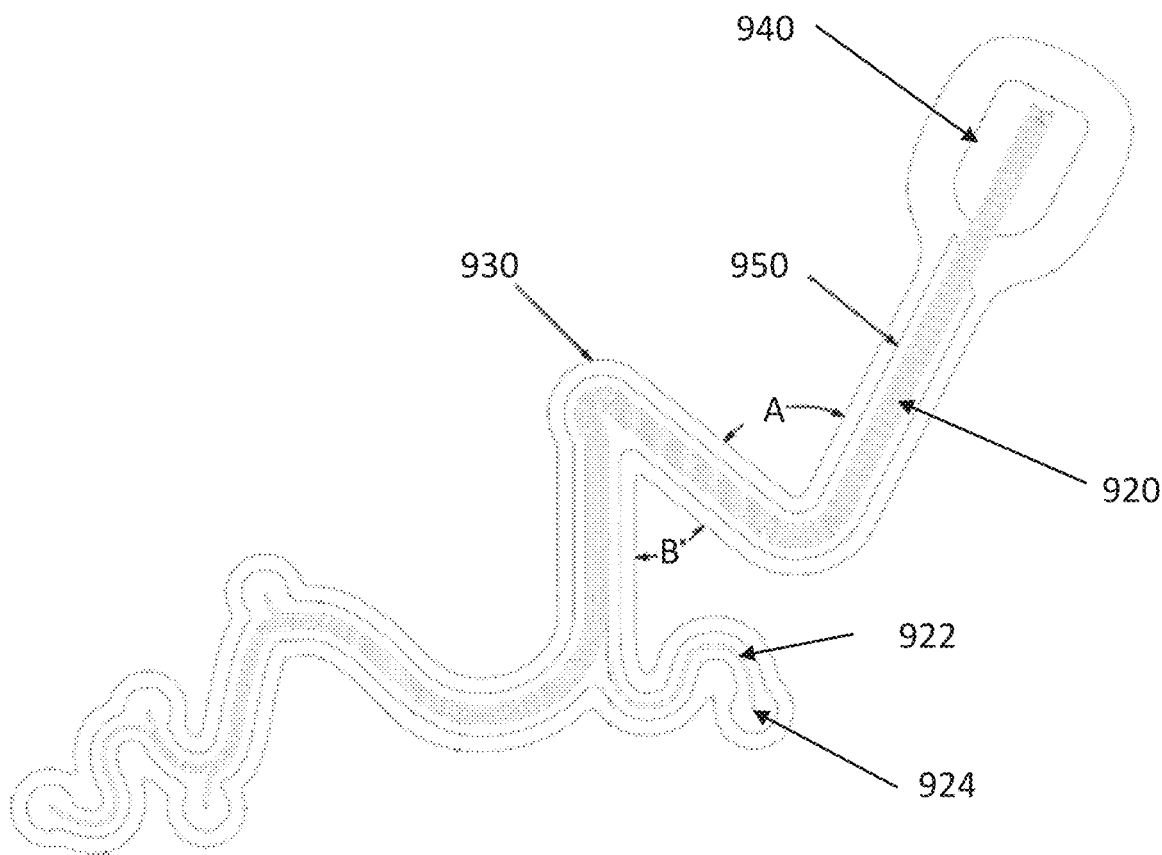
FIG. 9B is an illustrative schematic of components of an exemplary variation of a system for monitoring a user.

FIG. 9B shows a schematic depiction of an exemplary sensor arrangement 920 with a curved configuration, similar to that shown in FIG. 9A. In this variation, the sensor arrangement 920 includes a plurality of sensor leads, where the proximal end of each sensor lead is received by a housing 940. Each sensor lead in the arrangement includes a sensor (e.g., a temperature sensor) at a distal end of the lead. The sensor arrangement of FIG. 9B includes numerous curved portions. The curved portions may curved at any suitable angle to traverse to desired sensor locations. In FIG. 9B, the curved portions are configured so as to circumvent high flex areas of the heel region 916 to avoid excessive strain on the sensor leads. In the variation depicted in FIG. 9B, the sensor arrangement includes curves with angles A and B configured to curve around one or more high flex areas of the heel region 916 of the garment 910. Angle A may, for example, be between about 65 degrees and about 90 degrees, between about 70 degrees and about 80 degrees, or about 78 degrees. Angle B may, for example, be between about 40 degrees and about 60 degrees, between about 45 degrees and about 55 degrees, or about 51 degrees.

Although the sensor arrangements 920 in FIGS. 9A and 9B form a substantially S-shaped path, any curved configuration may provide a similar benefit of reducing the impacts of strain on the sensor arrangement, and circumventing areas of a garment that may experience high levels of flexion and/or strain. Further, the sensor arrangement may have a curved configuration along any suitable portion of the garment. Although FIG. 9A shows the curved portion of the sensor arrangement 920 as extending along the heel region 916 of the garment 910, the curved portion may be at any suitable location along the garment. For example, in some variations, the sensor arrangement may comprise a curvature over its entire path along the ankle region of the garment.

In some variations, sensor leads may be housed in a protective material. For example, in the variation shown in FIG. 9B, the sensor leads may be bundled and contained within protective, flexible film 950 (e.g., a plastic, such as a polyurethane film) (e.g., sealed between two layers of film 950). A protective film 950 may provide the benefit of protecting the sensors from damage and/or outside moisture, and may be waterproof or water-resistant. The sensor arrangement 920 of FIG. 9B may also be contained within a cover 930. The cover may couple the sensor leads to the garment 910, and direct the sensor leads along a path from the ankle region 914, to the sole region 912 of the garment 910. The shape of the film 950 and/or cover 930 may closely approximate the curved shape of the sensor arrangement 920. In some variations, the cover 930 may be a recessed portion or a cover portion of a garment, such as that of a sock or a shoe, for example.

Turning back to FIGS. 1A-1D, generally, the sensor leads 122 may be arranged to distribute the temperature sensors 124 among a variety of discrete target regions of the garment, so as to measure skin temperature at different locations of interest when the garment is placed on a user's foot. In some variations, measurement locations of interest may include locations typically experiencing high pressure when the user is active (e.g., walking or standing). For example, the sensor arrangement may be constructed so as to arrange the one or more temperature sensors on the sole region of the garment. In one exemplary variation, the temperature sensors 124 may include six temperature sensors. One temperature sensor 124a may be positioned in a first region of the garment configured to contact an Ossa digit of the foot, or toe. For example, the temperature sensor 124a may be configured to contact skin overlying the first Ossa digit ("big toe") of the foot. Three temperature sensors 124b, 124c, and 124d may be positioned in a second region of the garment configured to contact skin overlying the boundary of the phalanges and the metatarsals of the foot. For example, the temperature sensors 124b, 124c, and 14d may be configured to contact skin proximate the first (most medial) metatarsal, the third metatarsal, and the fifth metatarsal, respectively. Additionally, another temperature sensor 124e may be positioned in a third region of the garment configured to contact skin overlying the boundary of the metatarsals and the tarsals of the foot. Furthermore, another temperature sensor 124f may be positioned in a fourth region of the garment configured to contact skin overlying the heel of the foot. The configuration of temperature sensors may be biased for a left foot in instances in which the garment is configured to be placed on a left foot, while the configuration of temperature sensors may be biased for a right foot in instances in which the garment is configured to be placed on a right foot.

In other variations, the sensor arrangement may be constructed so as to additionally or alternatively arrange one or more temperature sensors on other regions of the garment (e.g., medial or lateral sides of a foot region of the garment, dorsal portion of a foot region of the garment, ankle region of the ankle, etc.).

Figure 2:
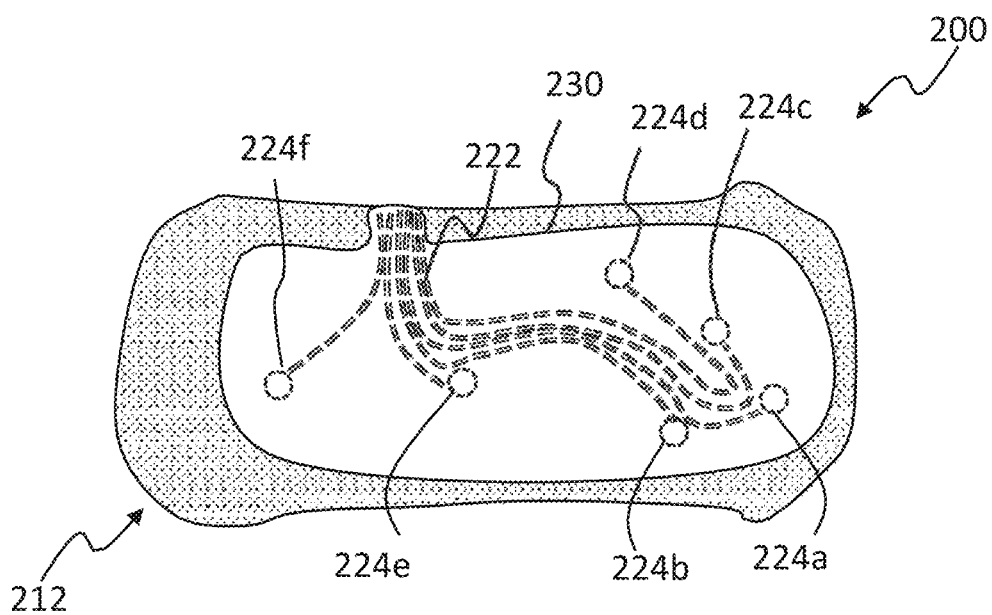
FIG. 2 is a bottom view of another exemplary variation of a system for monitoring a user.

In locating the temperature sensors to their respective measurement locations, the sensor leads 122 may traverse the sole region in a curved path which may, for example, provide additional strain relief to the sensor arrangement (e.g., the curved pattern can better withstand stretching, etc.). For example, the curved path may be generally "S"-shaped, serpentine, or other suitable non-linear path. In some variations, as shown in FIG. 1B, the distal end of one or more sensor leads 122 (and their temperature sensors) may diverge or branch from the sensor lead bundle such that the temperature sensor attached to a diverging sensor lead is independently positioned at a desired measurement location. Additionally or alternatively, at least a portion of the sensor lead bundle may traverse the sole region 112 between different measurement locations in series, such that at least some sensor leads are not substantially diverging or branching from the main bundle. For example, FIG. 2 illustrates a variation in which the bundle of sensor leads for temperature sensors 224a-224e navigates to five measurement locations in series, with individual sensor leads simply terminating at their respective sensors' measurement locations. In this example, some of the sensor leads may be shorter than others. In the example of FIG. 2, the sensor lead for temperature sensor 224f diverges from the main bundle of sensor leads, while the other sensor leads do not substantially diverge. It should be understood, however, that there are many suitable configurations in which the sensor leads traverse the sole region of the garment to position the temperature sensors at the desired measurement locations. For example, the distal ends of none, some, or all sensor leads (in any combination) may diverge from a main sensor lead bundle to position respective temperature sensors. Furthermore, none, some, or all sensor leads (in any combination) may navigate to measurement locations in series (in any permutation or order), in a non-diverging manner, to position respective temperature sensors.

Figure 10:
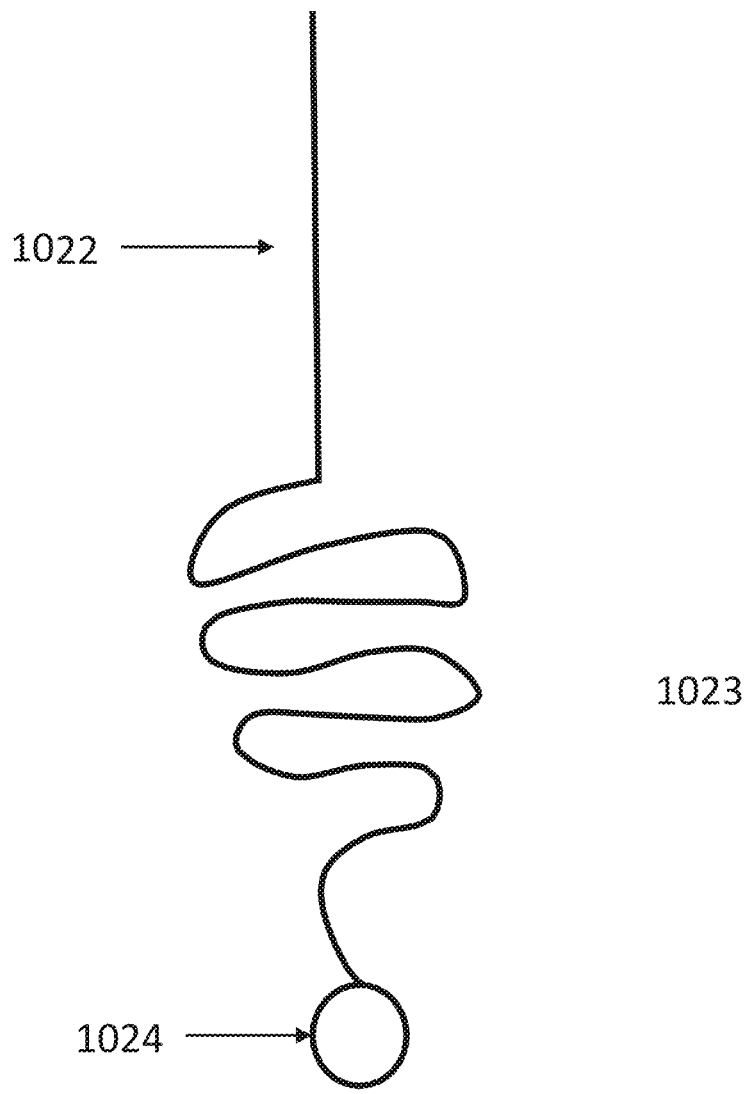
FIG. 10 is an illustrative schematic of a sensor of an exemplary variation of a system for monitoring a user.
Figure 11:
FIGS. 11-17 are a lower perspective view, a front view, a rear view, a right side view, a left side view, a top plan view, and a bottom plan view, respectively, of an exemplary variation of a garment.
Figure 12:
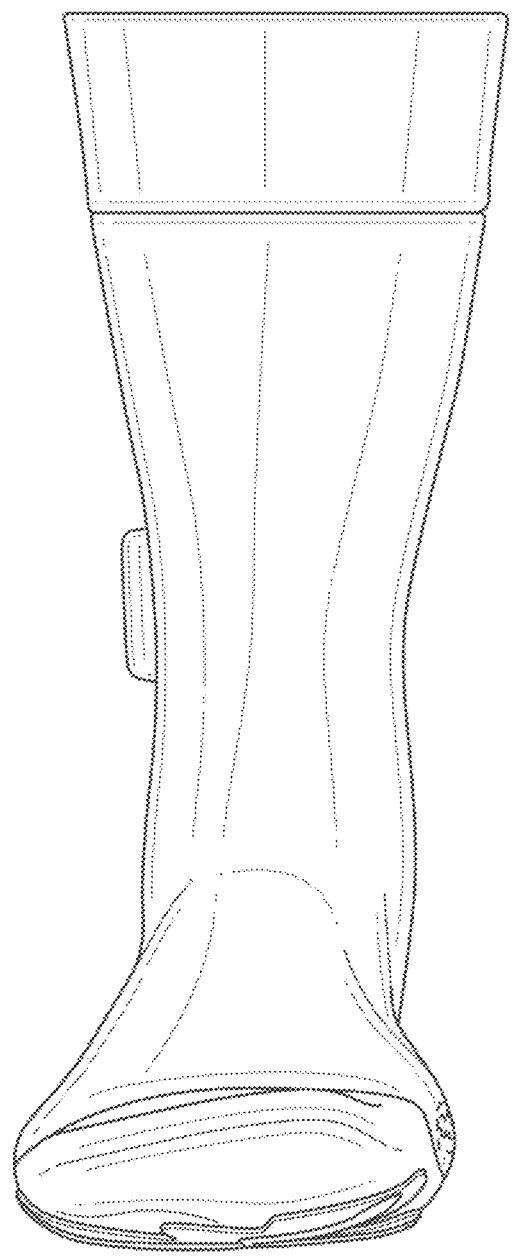
Figure 13:
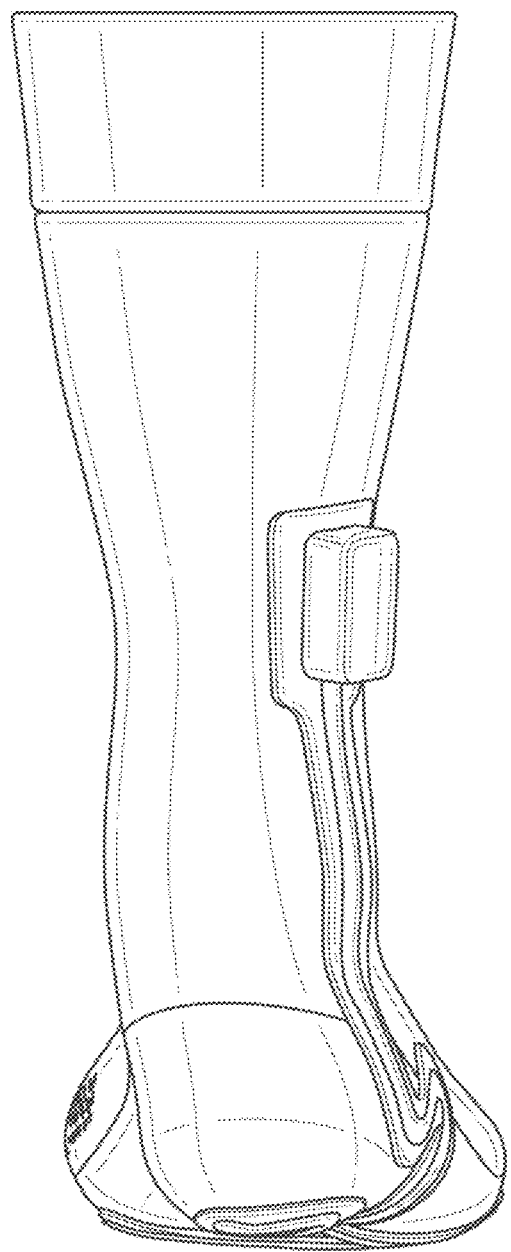
Figure 14:
Figure 15:
Figure 16:
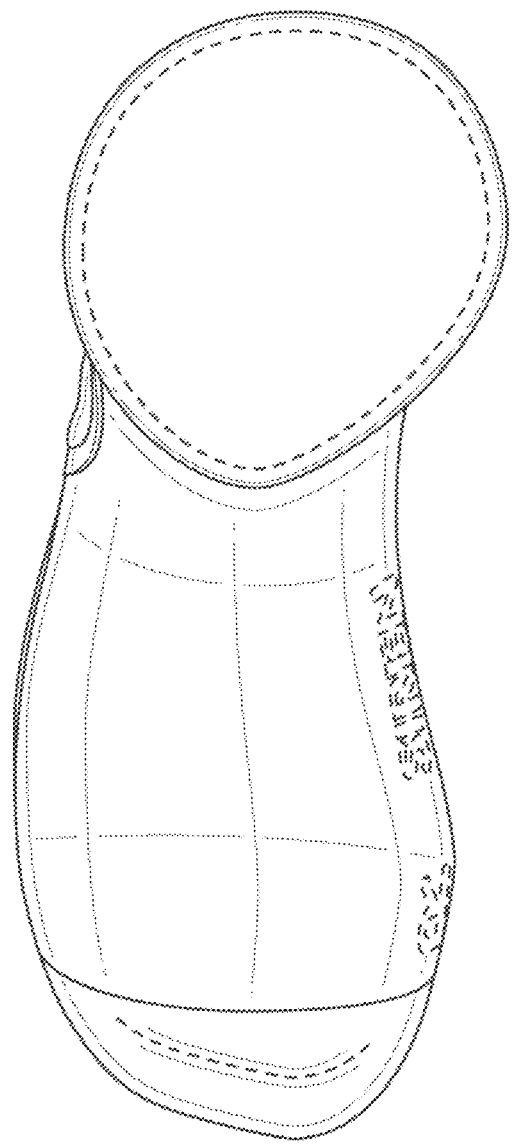
Figure 17:
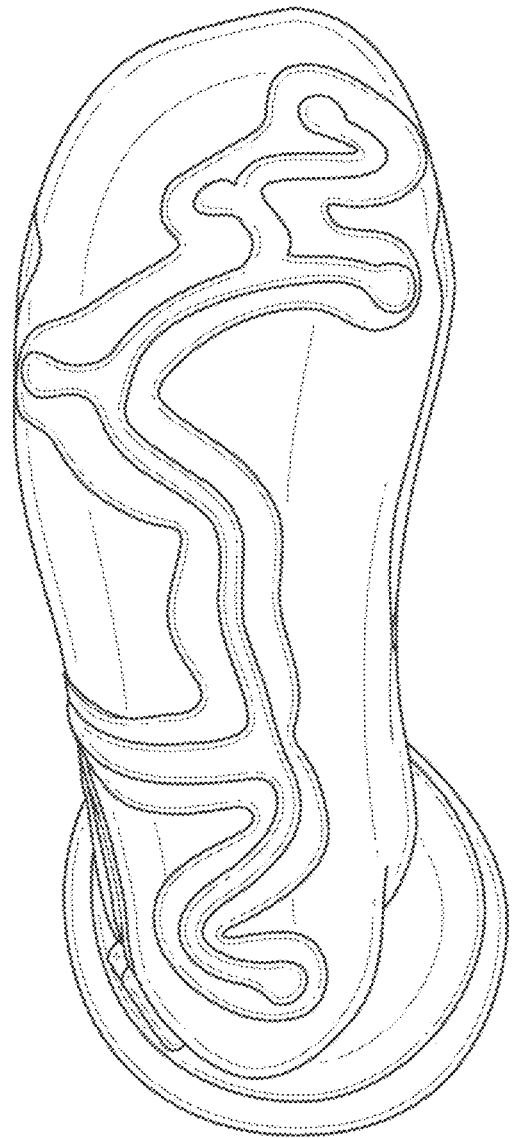
Figure 18:
FIGS. 18-24 are a lower perspective view, a front view, a rear view, a right side view, a left side view, a top plan view, and a bottom plan view, respectively, of another exemplary variation of a garment.
Figure 19:
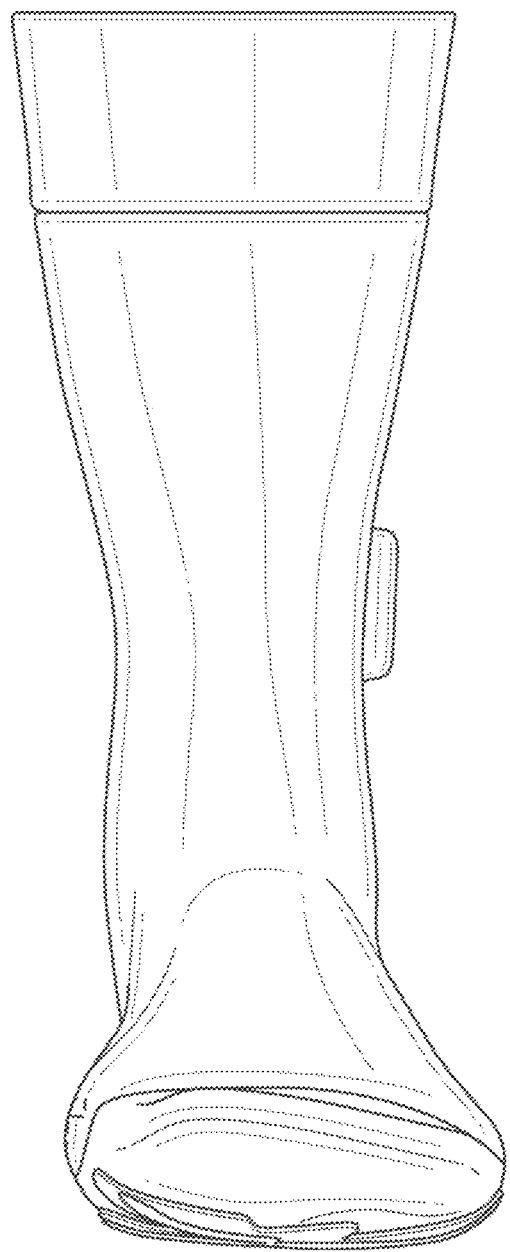
Figure 20:
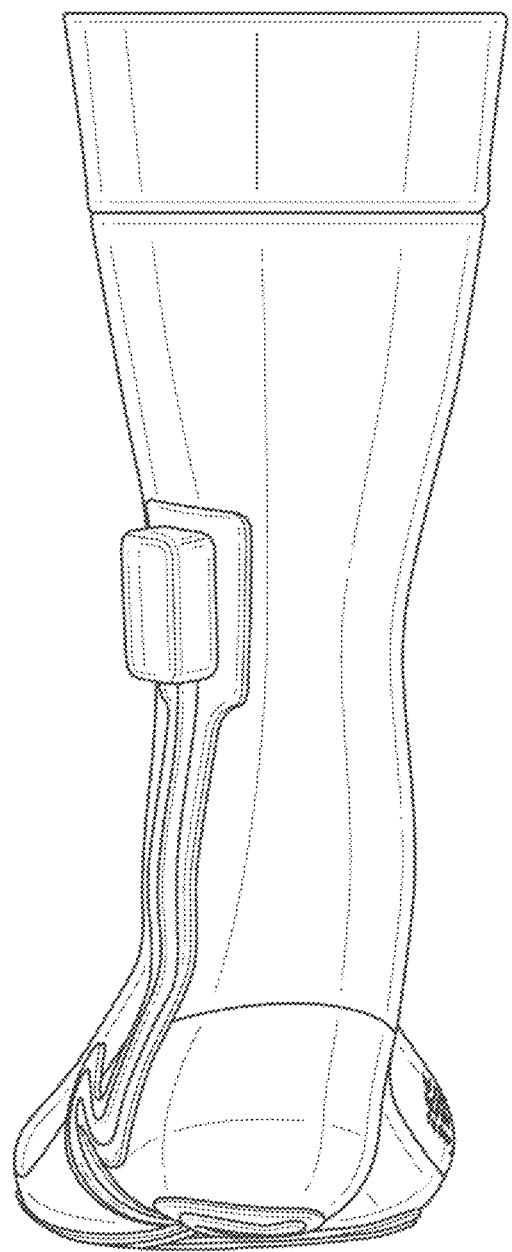
Figure 21:
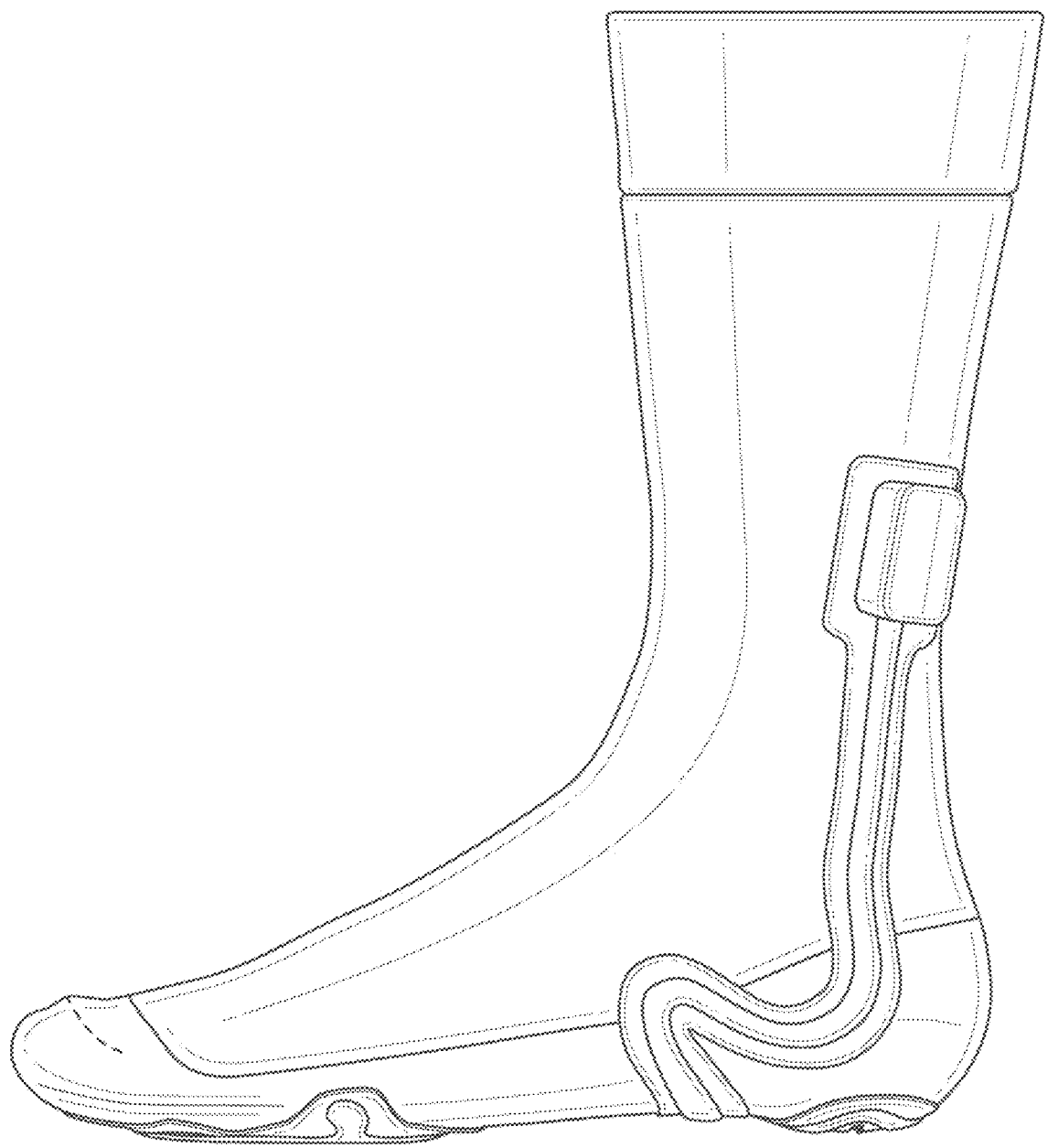
Figure 22:
Figure 23:
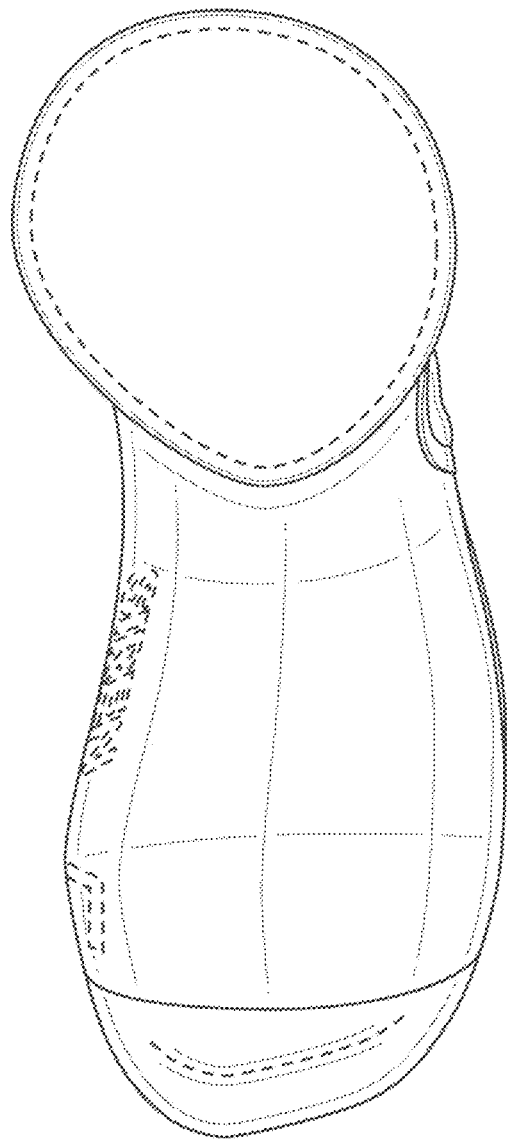
Figure 24:
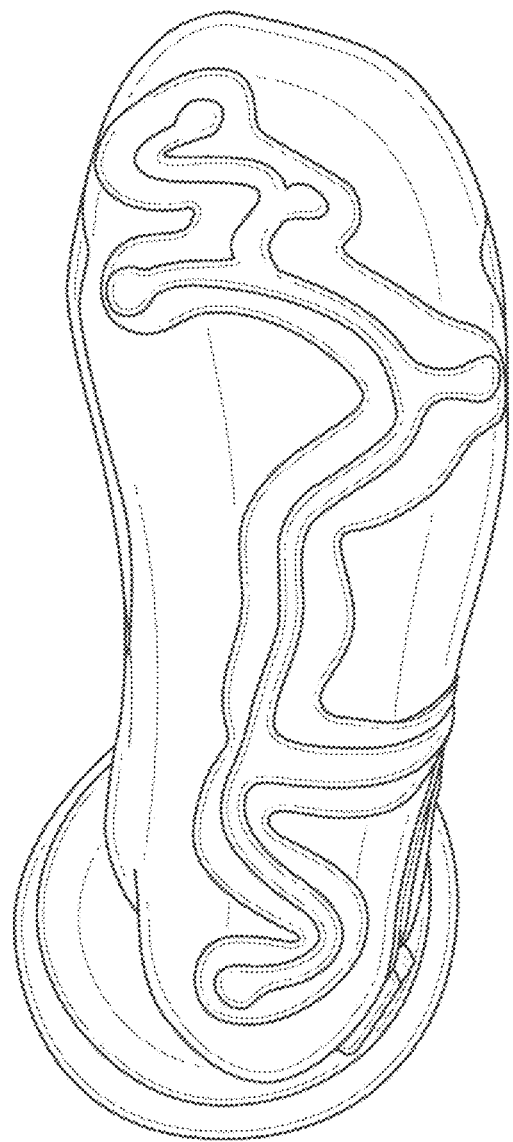
Figure 25:
FIGS. 25-31 are a lower perspective view, a front view, a rear view, a right side view, a left side view, a top plan view, and a bottom plan view, respectively, of another exemplary variation of a garment.
Figure 26:
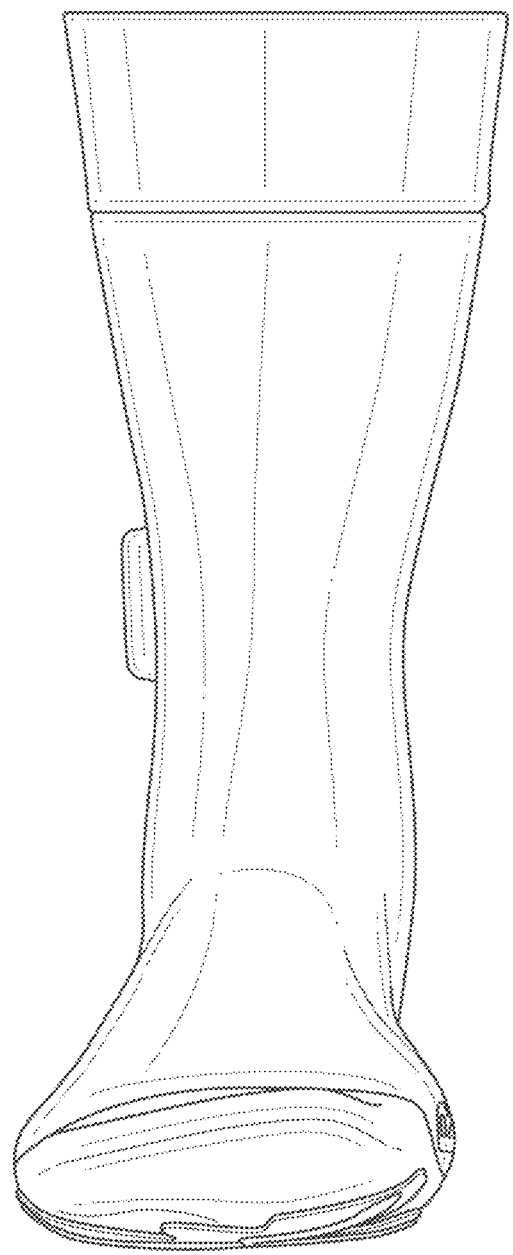
Figure 27:
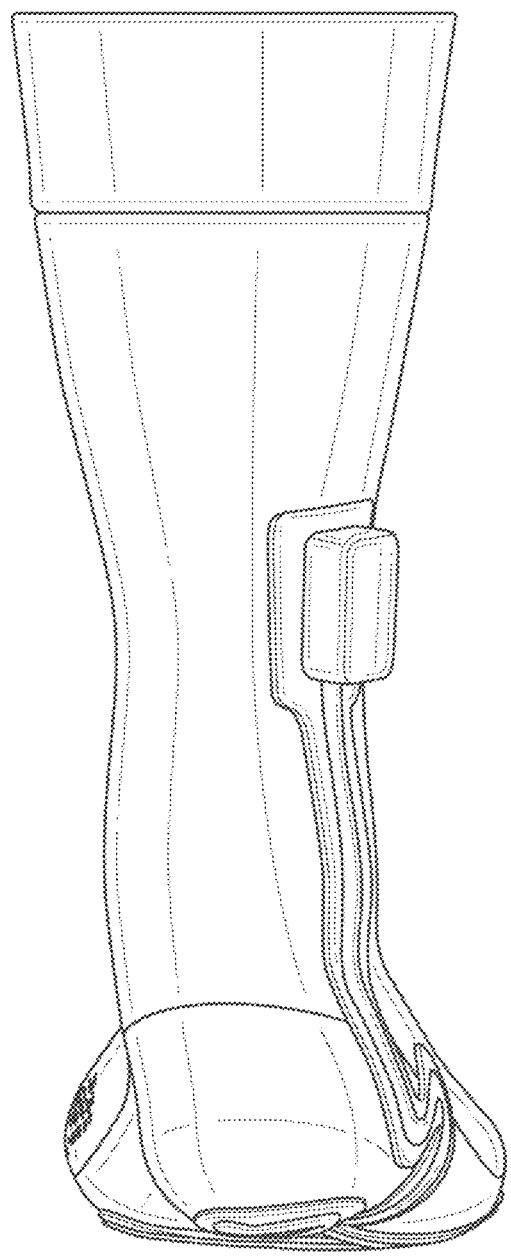

In some variations, a sensor lead may have a coiled or serpentine configuration at a distal end proximate to the sensor. For example, FIG. 10 is a schematic representation of a distal end of a sensor lead 1022 and a sensor 1024 coupled to the distal end of the sensor lead. In this variation, the sensor lead 1022 includes a serpentine configuration 1023 near the distal end. As described above, arranging the sensor leads in a curved configuration may provide strain relief to the sensor arrangement, and reduce the risk that a sensor lead will become damaged. In some variations, a serpentine configuration at a distal end of a sensor lead may be more tightly curved than the curvature of the sensor leads elsewhere. Sensor leads may be placed under higher levels of strain at their distal ends near sensors due to pressure and movement of the sensor. Thus, the distal end of the sensor leads may be more susceptible to breakage or other forms of damage than other portions of the sensor lead. Therefore, a curved portion such as a coiled or serpentine configuration at the distal end of the sensor lead near the sensor may be beneficial.

In some variations, the relative positions and orientations of some or all the sensor leads (and accordingly, the relative positions of the respective sensors) may be fixed with additional components. For example, once arranged in a configuration such as that described above, at least some of the sensor leads may be coupled to each other with epoxy or fasteners (e.g., ties, clips, etc.). Additionally or alternatively, at least some of the sensor leads may be collectively sealed together, such as sealed between multiple (e.g., upper and lower) layers of film or vacuum-sealed in a bag. Suitable film may be, for example, layers of polyurethane or other polymer. Accordingly, such sealing of the sensor arrangement may set the arrangement of sensor leads 122 (including the grouping or bundling of sensor leads, and the relative positions of the sensors) for us during assembly.

Cover

Generally, the system may further include at least one cover 130 coupled to the garment 110 such that the sensor arrangement and/or housing is located between the garment and cover. In some variations, the attachment of the cover 130 to the garment 110 may thereby secure the sensor arrangement and/or housing to the garment. The cover may be coupled to an internal surface of the garment, over a sensor arrangement and/or housing positioned on the inner surface of the garment. Alternatively, the cover may be coupled to an external surface of the garment, over a sensor arrangement and/or housing positioned on the outer surface of the garment.

In some variations, the cover may include a single piece. Alternatively, the cover may include multiple pieces that collectively enclose the sensor arrangement over the garment. For example, the cover may include an ankle cover portion sized and shaped to secure an ankle portion of the sensor arrangement 120 and/or the housing to the ankle region 114 of the garment, and a sole cover portion sized and shaped to secure a sole portion of the sensor arrangement 120 to the sole region 112. In this example, the ankle cover portion and sole cover portion may be coupled to each other and subsequently collectively coupled to the garment, or may individually and separately be coupled to the garment only. It should be understood that the cover may include any suitable number of cover segments that collectively cover the sensor arrangement and/or housing.

For example, as shown in FIGS. 1A and 1B, the cover 130 may be attached to the garment 110 around the perimeter of at least a portion of the sensor arrangement 120. In some variations, the shape of the cover may closely resemble the shape of the sensor arrangement 120 (e.g., slightly larger than the outline of the sensor arrangement, such as by a margin of at least about 0.5 cm).

Figure 3:
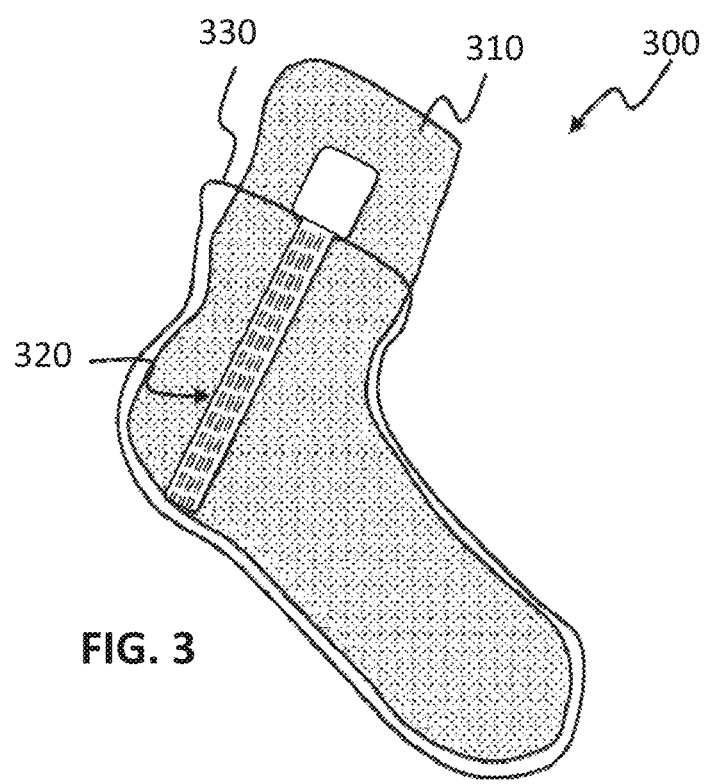
FIG. 3 is a side view of another exemplary variation of a system for monitoring a user.

Alternatively, in some variations, the cover may have any suitable shape and size larger than the outline of the sensor arrangement 120. For example, as shown in FIG. 2, a system 200 may include a cover 230 may be generally rectangular and larger than the overall area of the sensor arrangement on the sole region of the garment. In other variations, the cover 230 may be oval, circular, or other suitable shape. As another example, as shown in FIG. 3, a system 300 may include a cover 330 that provides a second layer to a substantial portion of the garment 310 (e.g., the sole region and at least part of the ankle region) such that the sensor arrangement 320 is layered between ("sandwiched" or laminated) between the garment and cover.

The cover may include any of various suitable materials. For example, the cover may include a textile (e.g., polyester, cotton, etc.) that is cut to a desired shape. In some variations, such a textile cover may be lined with a material suitable for heat sealing the cover to the garment, such as a thermoplastic material (e.g., thermoplastic polyurethane). Additionally or alternatively, the textile cover may be coupled to the garment with epoxy or other adhesive, sutures, and/or fasteners (e.g., rivets). In other variations, the cover may include an epoxy or other adhesive (e.g., silicone glue), or sewn threads (e.g., embroidery) that directly secures the sensor arrangement to the garment.

Additional aspects of manufacturing the user monitoring system described herein are described in further detail below.

Method for Making a User Monitoring System

Figure 4:
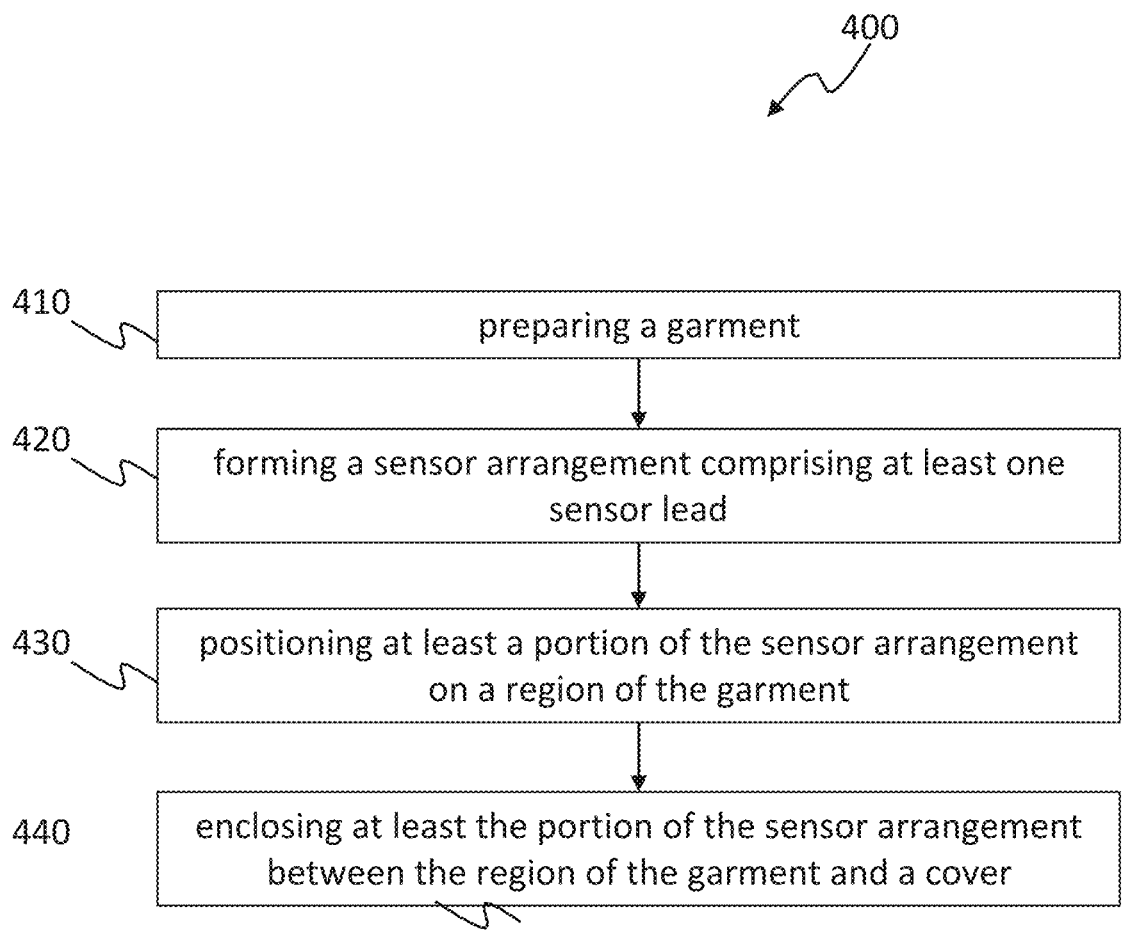
FIG. 4 is a flow chart schematic of an exemplary variation of a method for making a user monitoring system.

In some variations, as shown in FIG. 4, a method 400 for making a user monitoring system includes forming a sensor arrangement comprising at least one sensor lead (420), positioning at least a portion of the sensor arrangement on a region (e.g., sole region) of a garment (430), and enclosing at least the portion of the sensor arrangement between the region of the garment and a cover (440). In some variations, the method 400 may further include preparing a garment (410) to receive the sensor arrangement, as further described below, though in some variations the garment may be pre-prepared and already configured for receiving a sensor arrangement. Generally, the method 400 may be performed to make at least part of the systems described above for monitoring a user. Although the method is primarily described with reference to making a foot-borne garment such as a sock, it should be understood that variations of the method 400 may be used to make similar monitoring systems with other garments or for other body parts (e.g., slippers, insoles, gloves, pants, shirts, etc.).

Preparing the Garment

Figure 5:
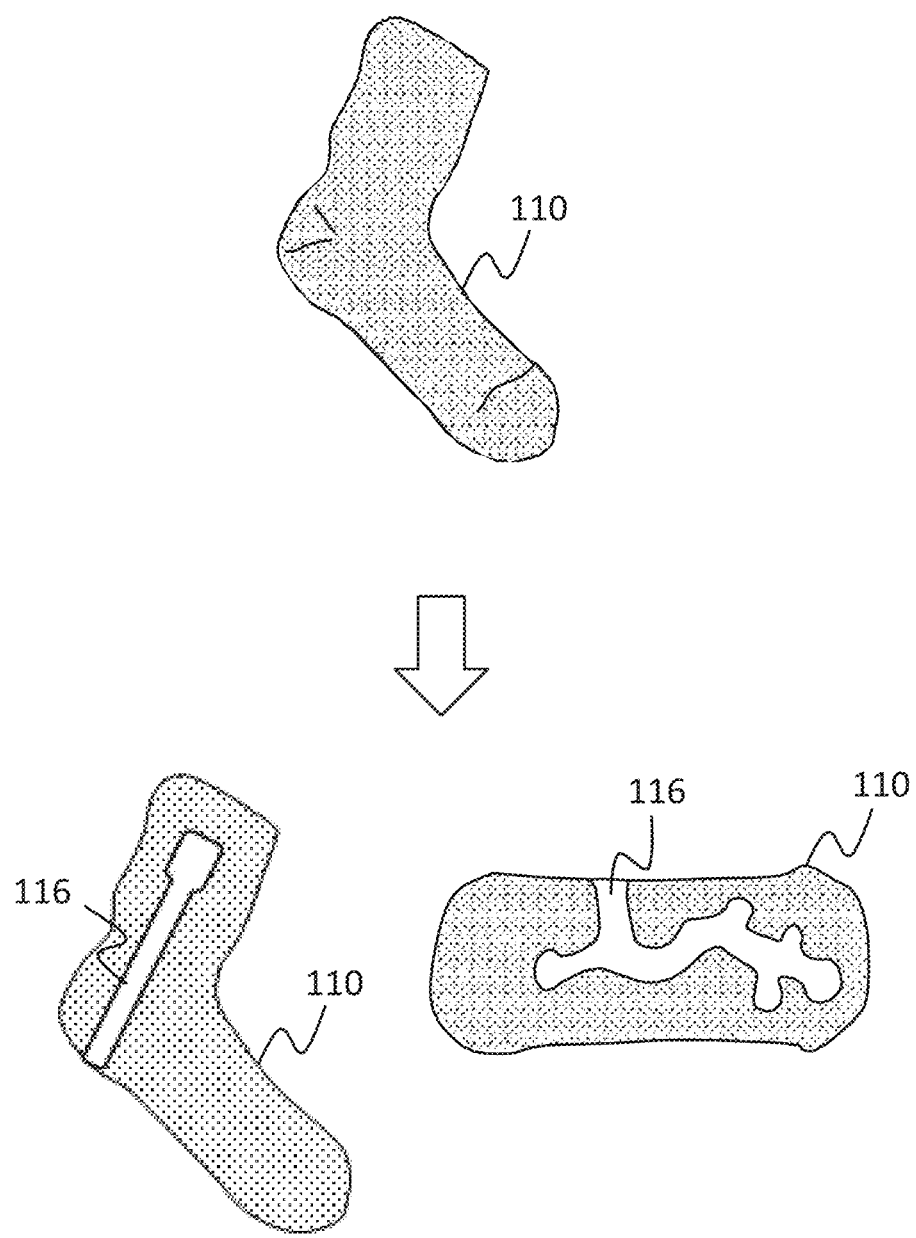
FIG. 5 is a graphical representation of a portion of an exemplary variation of a method for making a user monitoring system.

FIG. 5 generally illustrates aspects of preparing the garment (410). As shown in FIG. 5, a garment may be prepared by forming one or more recessed portions 116 of the garment 110, where the one or more recessed portions may be configured to receive the sensor arrangement and reduce the overall profile of the garment that otherwise would be increased as a result of the sensor arrangement. For example, the garment may include a plush material (e.g., terry knit) that can be thinned or cut shorter (e.g., with a cutting blade, scissors, a razor, and the like) in selected regions where a recessed portion is desired. In some variations, the one or more recessed portions 116 of the garment may be arranged on an internal (skin-contacting) surface of the garment. For example, the garment may be turned inside out to allow access to the internal surface of the garment, and the internal surface of the garment may be trimmed to form the recessed portions 116. The garment may remain inside out for positioning and coupling the sensor arrangement and cover to the internal surface of the garment as described below. In other variations, the one or more recessed portions 116 may be arranged on an external surface of the garment.

As shown in the variation of FIG. 5, the recessed portions 116 may generally resemble the footprint area or shape of the sensor arrangement (e.g., a branching pattern on the sole region of the garment 110, with diverging branches or lobes corresponding to sensor locations). However, the recessed portions 116 may have any suitable size and shape for receiving at least part of the sensor arrangement. Additional patterns for recessed portion are described above, for example.

Forming the Sensor Arrangement

Figure 6:
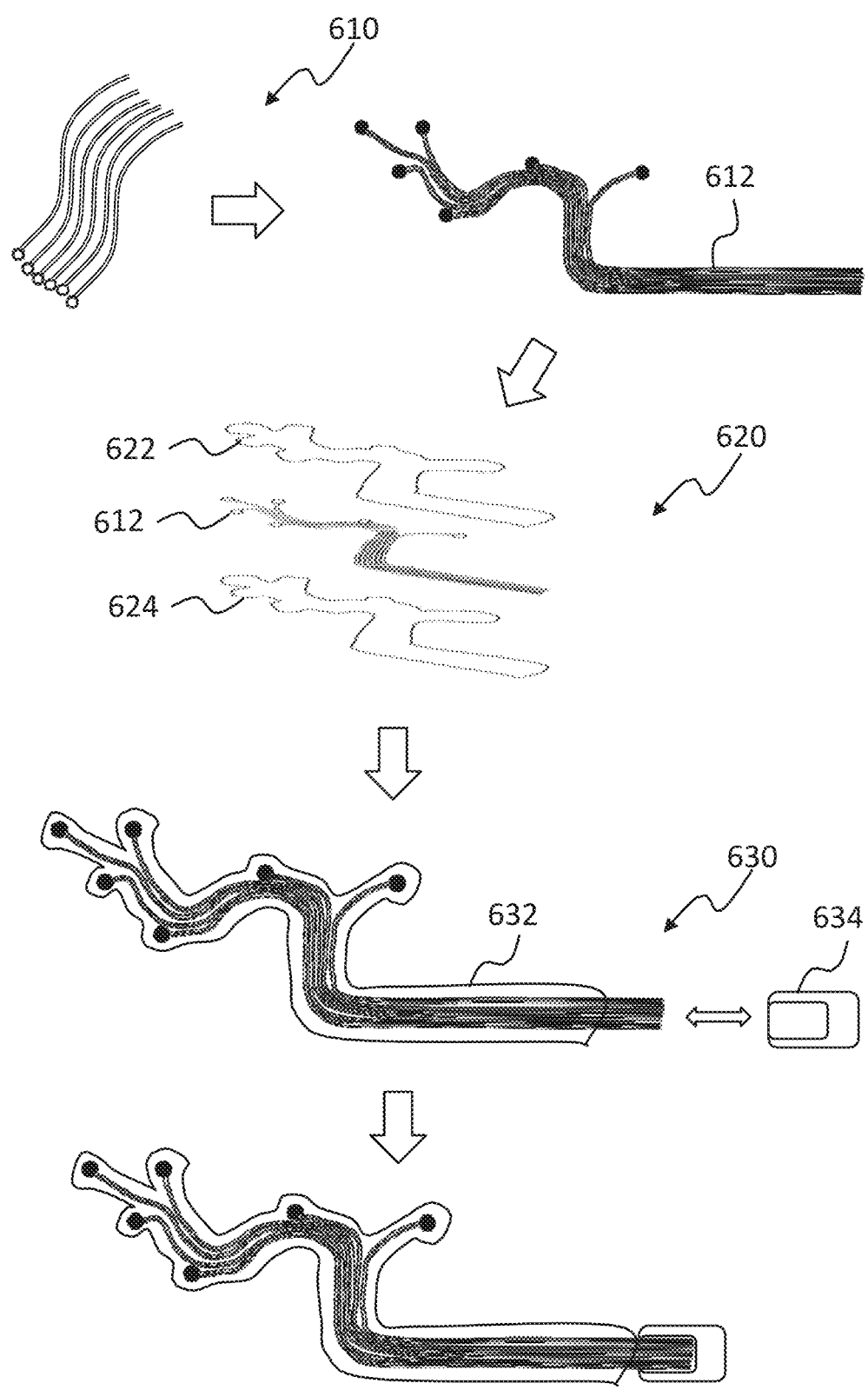
FIG. 6 is graphical representations of a portion of an exemplary variation of a method for making a user monitoring system.

FIG. 6 generally illustrates aspects of forming the sensor arrangement (420). For example, the sensor arrangement may be formed at least in part by arranging individual sensor leads into a bundle (610) or other grouping. The bundle may, for example, be a flattened bundle with a low profile (e.g., sensor leads arranged side-by-side in a single layer). The bundle may be shaped with any suitable number of sensor leads with a distal end that diverges from the bundle for separately positioning a temperature sensor coupled to the distal end of the sensor lead. Various examples of sensor lead configurations are described in further detail above.

There are several suitable methods for arranging the sensor leads into a bundle 612. In one exemplary variation, the sensor leads may be arranged (e.g., manually or automatically with tooling, etc.) with the assistance of a fixture having one or more open channels (e.g., groove) that is shaped to resemble the desired sensor lead layout. Sensor leads may be placed into the open channels, which gathers and shapes the sensor leads into the desired shape. Similarly, in another exemplary variation, the fixture may include one or more closed channels (e.g., lumens) shaped to resemble the desired sensor lead layout. In this variation, sensor leads may be fed longitudinally into the closed channels, which similarly gathers and shapes the sensor leads into the desired shape. In yet another exemplary variation, the sensor leads may be manually arranged in a free-form manner on a surface. The surface may include, for example, an outline or reference markers guiding placement of the sensor leads.

In some variations, after the sensor leads are arranged into a bundle 612 or other suitable pattern, the arrangement may be sealed or otherwise set, in order to fix the relative positions of the sensor leads. For example, as shown in FIG. 6, at least a portion of the arranged sensor leads may be laminated between layers of thermoplastic film 622 and 624 (e.g., thermoplastic polyurethane, or other thermoplastic), such as with heat sealing. Other examples of fixing the sensor arrangement include sealing in a bag (e.g., vacuum sealing), and coupling sensor leads together with adhesive, fasteners, threads, etc.

The proximal ends of the sensor leads in the sensor arrangement may remain exposed (unsealed) so as to allow electrical connection for sensor data communication. As shown in FIG. 6 for example, the proximal ends of the sensor leads may be connected (e.g., soldered) to pins of one or more processors in a housing 634 or other suitable connector. The connection between the sensor leads and the processors may be protected by applying a substance (e.g., UV glue, silicone glue, putty, etc.) over the electrical connection, and/or otherwise the connection region with the housing.

Forming a Cover

In some variations, the cover may include a flexible material that may formed into a suitable shape for covering the sensor arrangement and coupling to the garment. The cover may include a single or multiple portions. In an exemplary variation, the cover may include a material conducive to heat sealing, such as a textile (e.g., polyester or other suitable fabric) lined with a thermoplastic (e.g., thermoplastic polyurethane). However, in other variations the cover may include a textile otherwise coupleable to the garment via epoxy, fasteners, etc. Generally, a textile cover may be formed by cutting the cover shape from the textile (e.g., with scissors, laser cutting, etc.). Accurate cutting of the cover shape may be facilitated with a template, jig, and/or other suitable tooling. Suitable exemplary cover shapes are described in further detail above.

Assembling the Garment and Sensor Arrangement

Figure 7:
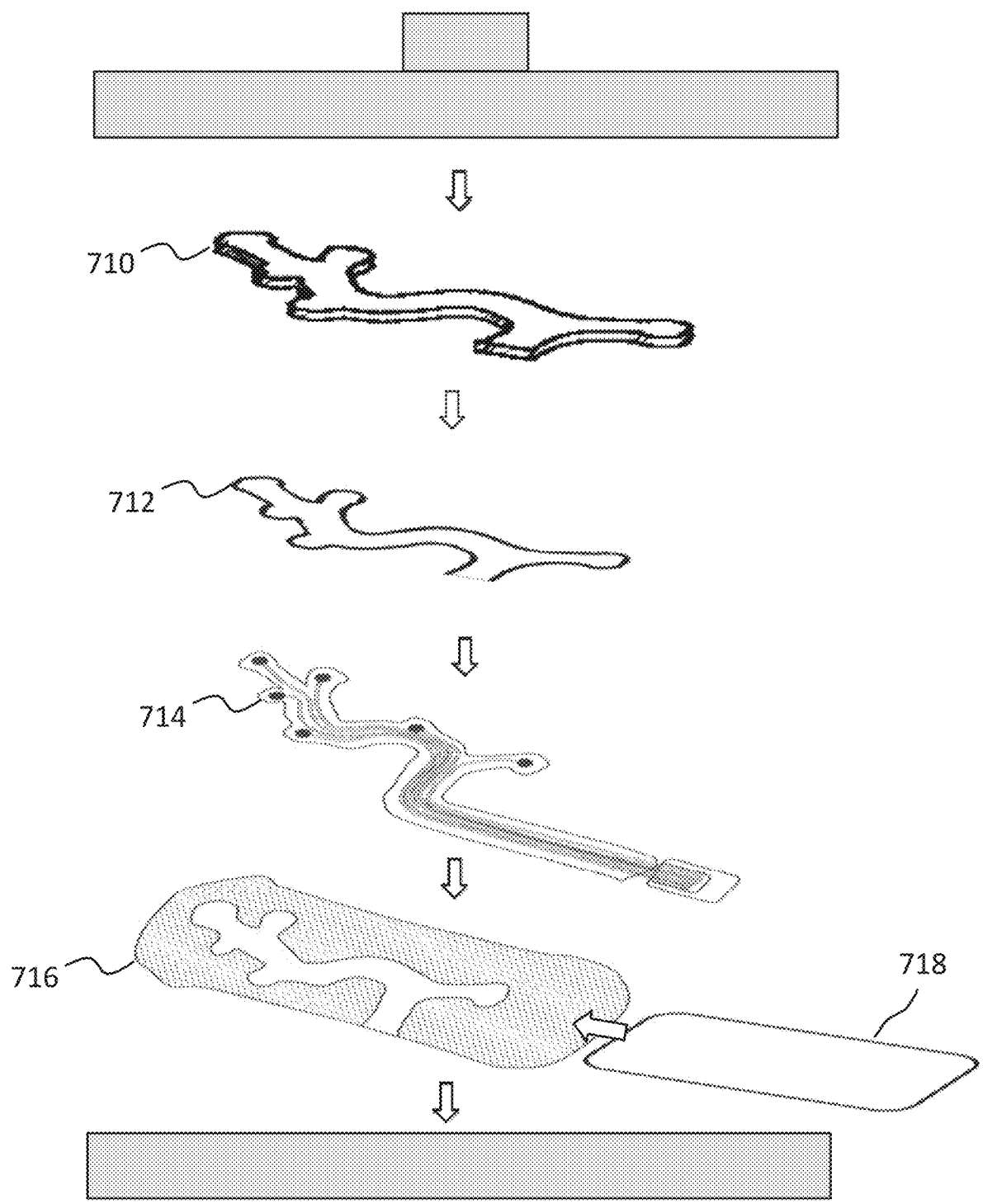
FIGS. 7 and 8 are graphical representations of a portion of an exemplary variation of a method for making a user monitoring system.
Figure 8:
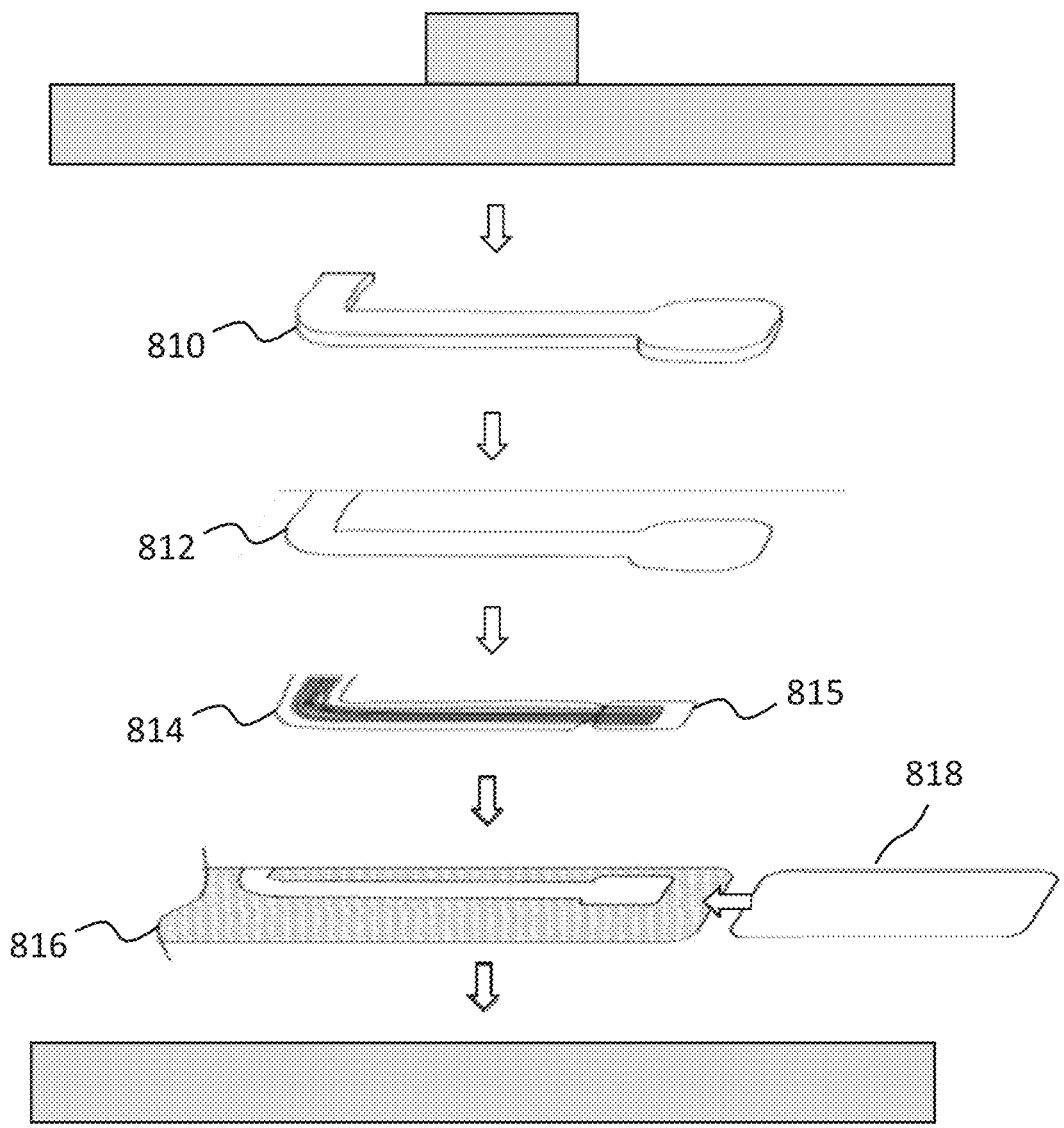

FIGS. 7 and 8 generally illustrate aspects of one variation of assembling the garment and the sensor arrangement. Specifically, FIG. 7 illustrates an exemplary process of enclosing the sensor arrangement between a sole region of the garment and a cover lined with a thermoplastic or similar material suitable for heat sealing. At least the sole region of the garment 716, a sole portion of the sensor arrangement 714, and a sole portion of the cover 712 may be stacked and aligned such that the sole portion of the sensor arrangement is contained between the garment and cover.

Various tooling apparatus may be added to the stack of system components. A forming block 710 may be placed over the cover 712, where the forming block 710 has a contact surface defining where the heat sealing will be applied. The forming block 710 may include a raised outer edge resembling the perimeter of the sensor arrangement (with additional sufficient margin, such as about 0.5 cm or greater). The forming block 710 may include a recessed portion corresponding to the shape of the sensor arrangement (or a recessed area at least as large as the sensor arrangement), such that the forming block protects the sensor arrangement from damage during subsequent compression of the assembled stack. Furthermore, in some variations, a heat-conductive model insert 718 may be inserted into the garment such that is provides a backing behind the sensor arrangement. The model insert 718 may, for example, be made of steel.

In order to heat seal the cover to the garment, it may be beneficial to flatten the garment, for example, to prepare for stacking of the system components used in heat sealing as described above. The garment may be flattened in any suitable manner. For example, the garment may be flattened from top to bottom, such that the sole portion of the garment is stacked on top of the ankle portion. In another variation, the garment may be flattened from side to side, such that the left side of the garment is stacked on top of the right side, or vice versa. Flattening the garment from side to side in preparation for heat sealing may provide the benefit of avoiding the creation of a fold or crease in the ankle region of the garment.

Heat and compression may be applied to the assembled stack of system components and tooling apparatus. For example, the model insert 718 may be heated (e.g., via an accessible portion of the model insert). Simultaneously, the stack may be compressed (e.g., with a clamp, vise, or similar device), such that heat from the model insert 718 induces sealing between the thermoplastic lining of the cover and the garment. As an addition or alternative to heat and compression, the cover may be coupled to the garment in other suitable ways such as by sewing or with fasteners. Following this process, the sensor arrangement 714 is enclosed between the sole region of the garment 716 and the cover 712.

FIG. 8 illustrates an exemplary process of enclosing the sensor arrangement and/or housing between an ankle region and the cover. Generally, this process may be similar to the process described above with reference to FIG. 7, except the assembled stack of system components includes an ankle region of the garment 816, an ankle portion of the sensor arrangement 814 and/or housing 815, and an ankle region of the cover 812 that are aligned such that the ankle portion of the sensor arrangement is contained between the garment and the cover. The forming block 810 may include a raised outer edge resembling the perimeter of the sensor arrangement and/or housing (with additional sufficient margin), and a recessed portion to protect the sensor arrangement during compression. Similar to that described above, heat and compression may be applied to the assembled stack. As an addition or alternative to heat and compression, the cover may be coupled to the garment in other suitable ways such as by sewing or with fasteners. Following this process, the sensor arrangement 814 is enclosed between the ankle region of the garment 816 and the cover 812.

In some variations, the model insert may be omitted from the stack. In variations, any other rigid backing, such as a flat workspace surface, may support the compression and/or provide heating. Furthermore, although the processes of FIGS. 7 and 8 are shown as separate steps, if should be understood that the garment may be arranged in a manner that allows these heat sealing processes to occur substantially in parallel.

Finally, if the garment was turned inside out to facilitate assembly of the sensor arrangement, the garment may be everted again to restore the garment to the intended wearable state.

Examples

FIGS. 9A, and 11-38 depict multiple variations of a system for monitoring a user, including a garment configured to be placed on the foot of a user. The exemplary garments include a sensor arrangement extending from the ankle region of the garment to the sole region of the garment, where each sensor lead in the arrangement is coupled to a sensor on the sole region of the garment configured to measure the temperature of the foot of a user. The sensor arrangement of the garment depicted in FIGS. 9A, and 11-38 includes a curved configuration along the heel region of the garment. The garments depicted in FIGS. 9A, and 11-38 may be manufactured using any suitable methods, such as those described above. For example, the sensor arrangement may be coupled to the garment by situating the sensor arrangement within a cover, and heat sealing the cover to the garment. The sensor arrangement may also be placed in a protective film prior to be coupled to the garment, as described above. The housing may be attached to the garment in any suitable manner (e.g. by placing the housing in a cover and heat sealing the cover to the garment, using an adhesion mechanism such as a snap fit, etc.). In FIG. 9A, the housing 940 is a box-like component with a rectangular cross section located on the ankle region 914 of the garment 910, however, the housing may include any suitable size, shape, and location. The proximal ends of sensor leads may be coupled to the housing in any suitable manner (e.g. using an epoxy to couple the leads and seal them to the housing).

Figure 28:
Figure 29:
Figure 30:
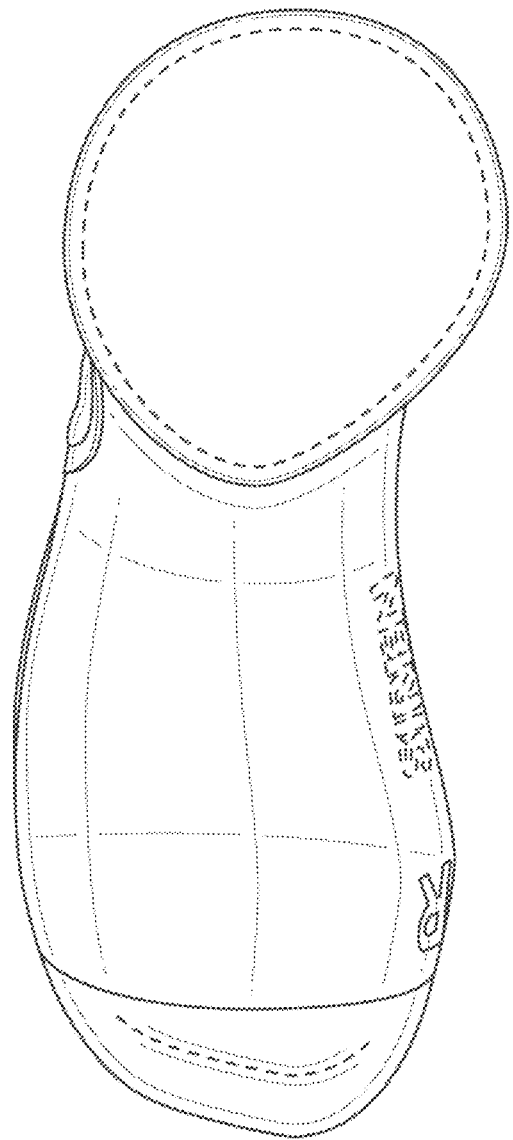
Figure 31:
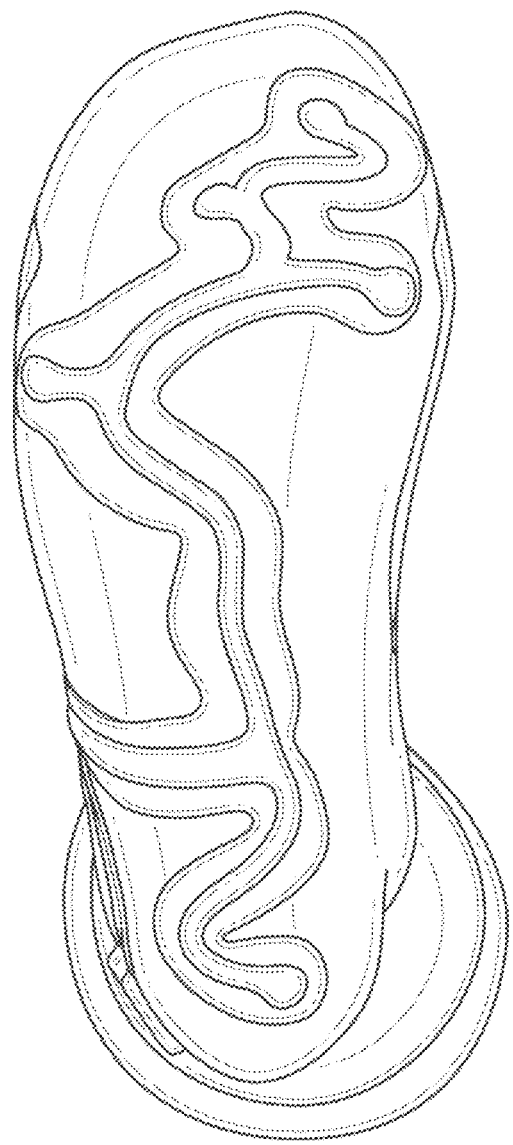
Figure 32:
FIGS. 32-38 are a lower perspective view, a front view, a rear view, a right side view, a left side view, a top plan view, and a bottom plan view, respectively, of another exemplary variation of a garment.
Figure 33:
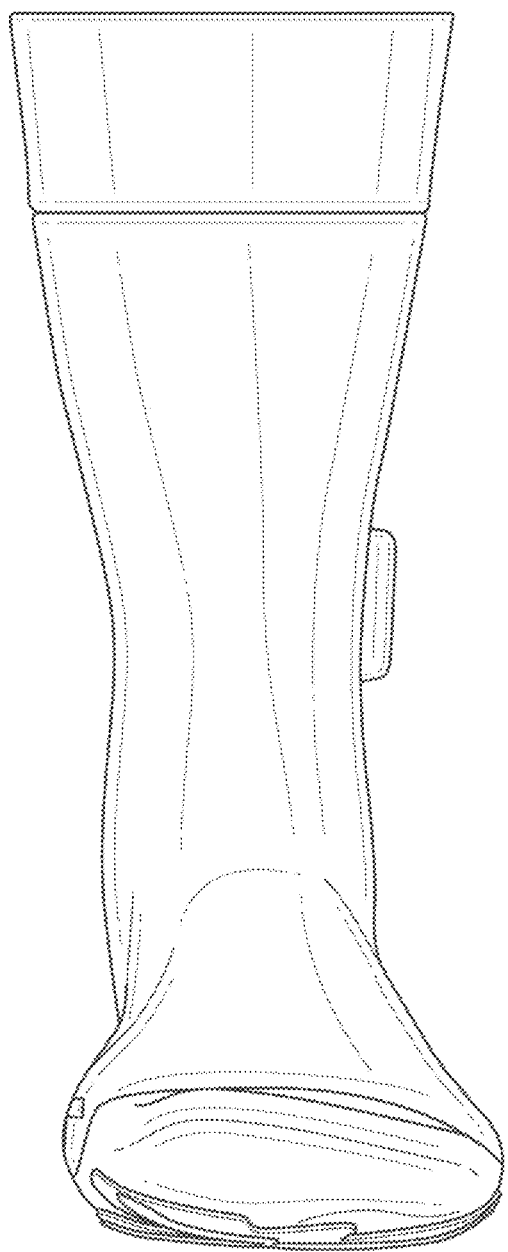
Figure 34:
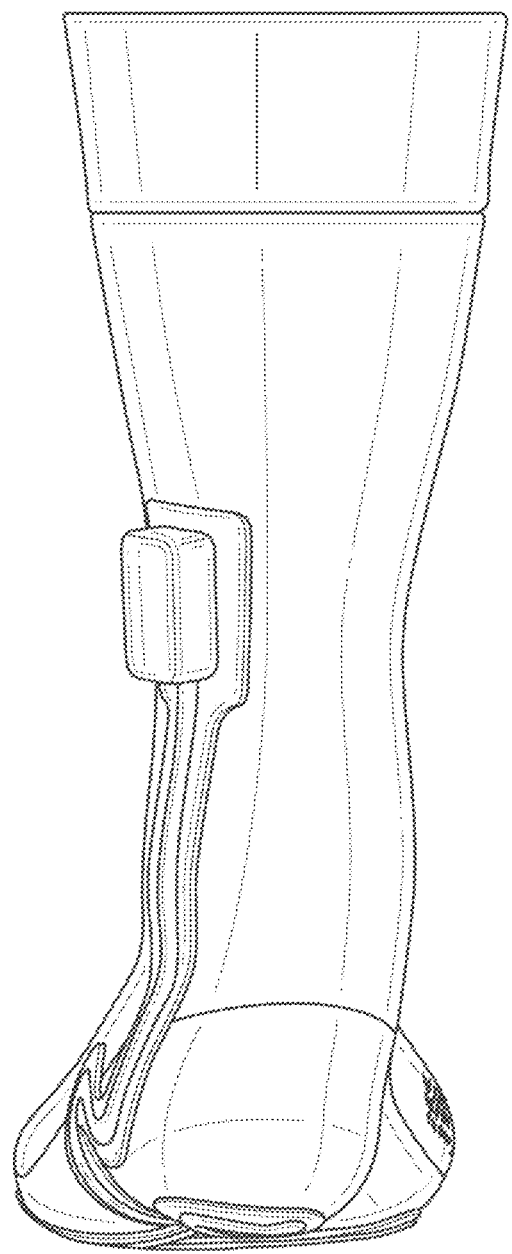
Figure 35:
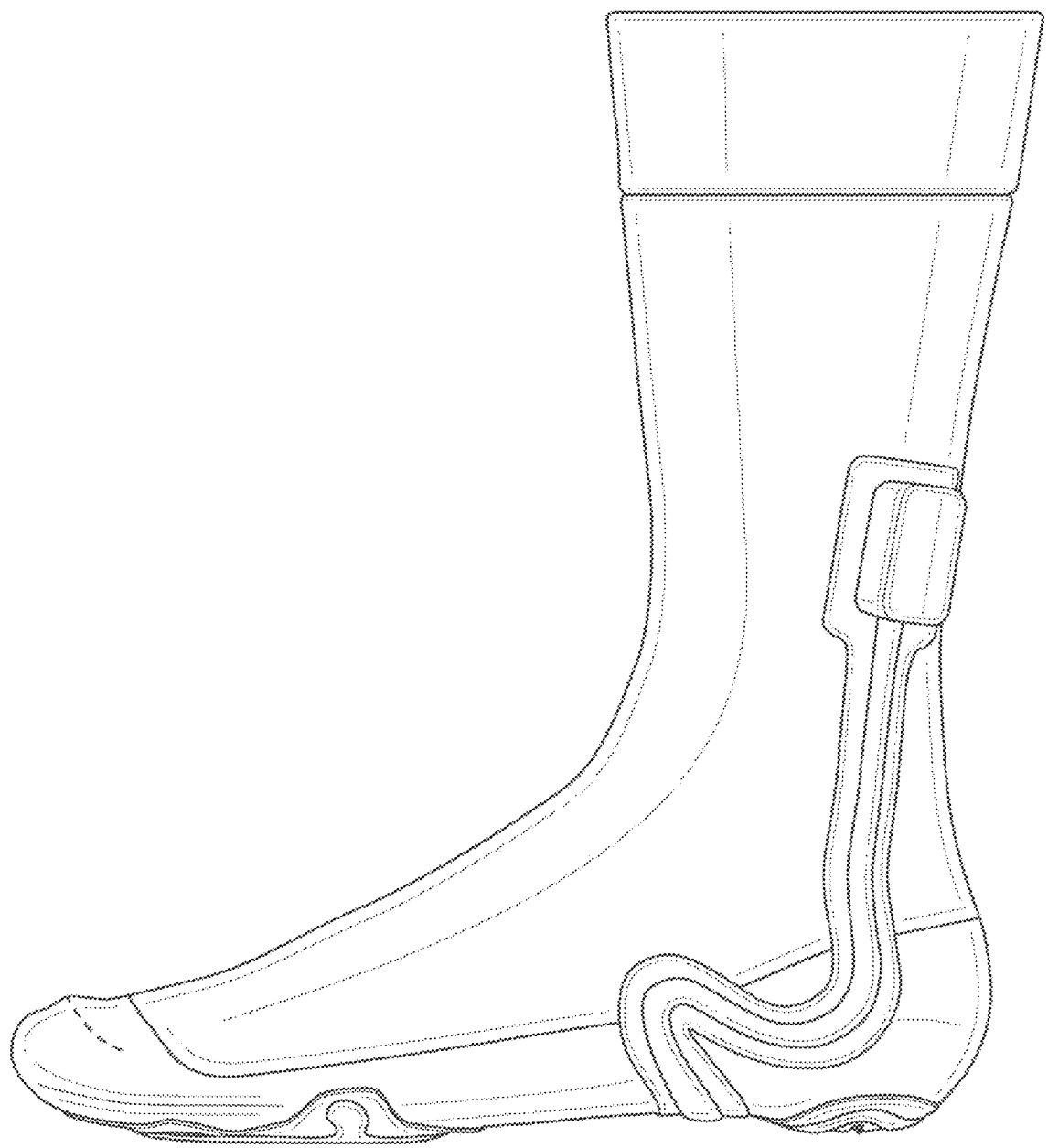
Figure 36:
Figure 37:
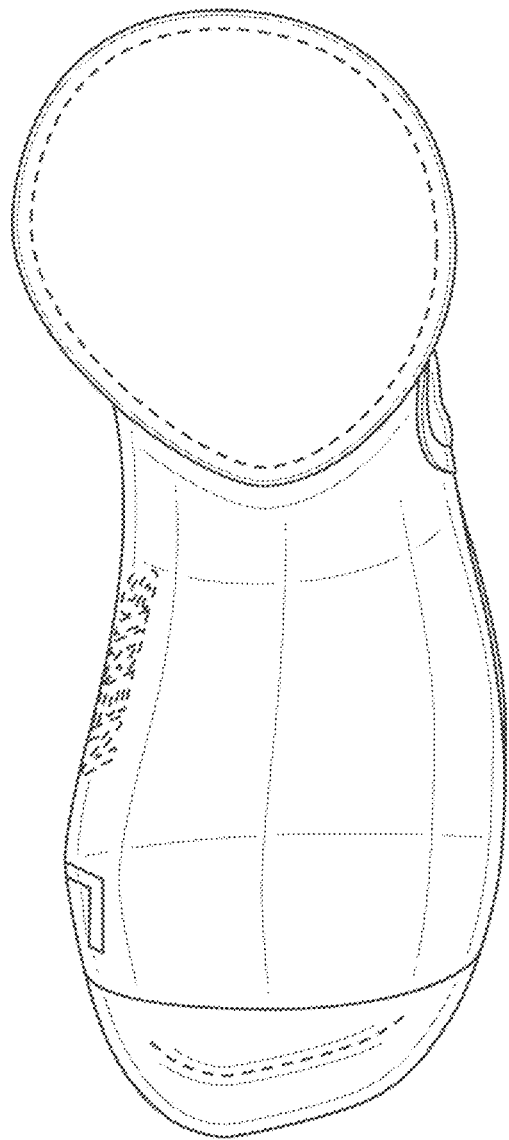
Figure 38:
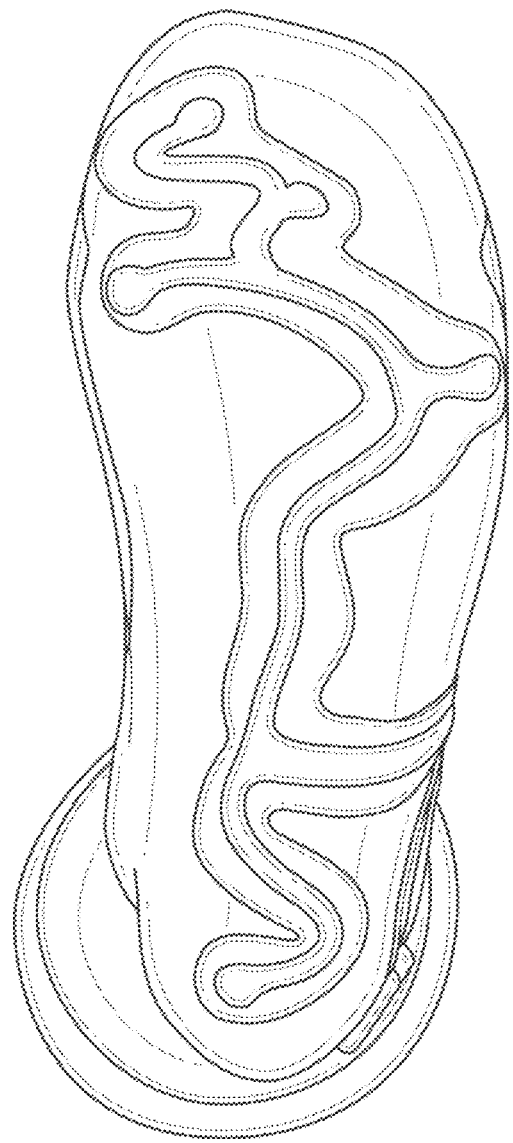

In some variations, garments may comprise markings to indicate which foot of a user the garment is intended to be worn on. In other variations, garments may not comprise a marking indicating what foot the garment is intended to be worn on. For example, FIGS. 11-17 depict various views of a garment (with optional foot-designator marking) configured to be worn on a right foot, and FIGS. 18-24 depict various views of a garment (with optional foot-designator marking) configured to be worn on a left foot. FIGS. 25-31 depict various views of a garment configured to be worn on a right foot, where the garment includes a foot-designator marking ("R") indicating that the garment is intended to be worn on a right foot. FIGS. 32-38 depict various views of a garment configured to be worn on a left foot, where the garment includes a foot-designator marking ("L") indicating that the garment is intended to be worn on a left foot. The foot-designator marking may be adhered to the garment in any suitable manner. For example, a marking such as an "R" or an "L" (as depicted in FIGS. 28 and 36, for example) indicating to a user what foot the garment is intended to be worn on may be knitted or embroidered into the garment, may comprise a patch sewn onto the garment or otherwise adhered to the garment, a decal ironed or otherwise adhered to the garment, may be made using fabric dye, etc.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated. It is intended that the following claims and their equivalents define the scope of the invention.

The invention claimed is:

1. A system for monitoring a user, the system comprising:
a sock configured to be worn on a foot of the user;
a cover coupled to a portion of the sock;
a sensor arrangement between the sock and the cover, the sensor arrangement comprising at least one sensor to measure at least one parameter associated with the foot of the user; and
an electronics housing between the sock and the cover, wherein the cover is sealed to the sock around a perimeter of the sensor arrangement and the housing.

2. The system of claim 1, wherein the sock comprises a recessed portion for receiving at least a portion of the sensor arrangement.

3. The system of claim 1, wherein the at least one sensor is arranged on a sole region of the sock at a location selected from an ossa digit region of the sock, between a phalange region and a metatarsal region of the sock, between the metatarsal region of the sock and a tarsal region of the sock, and a heel region of the sock.

4. The system of claim 1, wherein the cover is sealed to a sole region of the sock.

5. The system of claim 1, wherein the cover comprises a textile.

6. The system of claim 1, wherein the electronics housing encloses a proximal portion of the sensor arrangement.

7. The system of claim 1, wherein the electronics housing comprises at least one of a controller, a wireless communication module, a power supply, and a memory.

8. The system of claim 7, wherein the electronics housing comprises the controller, wherein the controller operates in an inactive state in response to an indication that the sock is not being worn by the user, and wherein the controller operates in an active state in response to an indication that the sock is being worn by the user.

9. The system of claim 1, wherein the sensor arrangement comprises a plurality of sensor leads, each sensor lead coupled to a respective sensor.

10. The system of claim 9, wherein the sensor leads are arranged in a flattened bundle traversing the sock.

11. The system of claim 10, wherein the bundle is shaped to follow a curved path.

12. The system of claim 11, wherein the curved path comprises a serpentine portion.

13. The system of claim 12, wherein the serpentine portion is on a sole region of the sock.

14. The system of claim 1, wherein the at least one sensor comprises a temperature sensor.

15. The system of claim 1, wherein the at least one sensor comprises a pressure sensor.

16. The system of claim 1, wherein the at least one sensor comprises at least one selected from the group consisting of a moisture sensor, a strain sensor, a weight sensor, a muscle activity sensor, a motion sensor, and an orientation sensor.

17. The system of claim 1, wherein the cover is heat sealed to the sock around the perimeter of the sensor arrangement and the housing.

18. The system of claim 1, wherein the sensor arrangement traverses a heel region of the sock in a curved configuration.

19. A system for monitoring a user, the system comprising:
a sock, having a sole region and an ankle region, configured to be worn on a foot of the user;
a cover coupled to a portion of the sole region and a portion of the ankle region of the sock;
a sensor arrangement between the sock and the cover, the sensor arrangement comprising at least one sensor to measure at least one parameter associated with the foot of the user; and a housing within the ankle portion and between the sock and the cover, wherein the cover is sealed to the sock at a perimeter of the sensor arrangement and the housing.

* * * * *